(12) United States Patent
Kim

(10) Patent No.: US 11,744,972 B1
(45) Date of Patent: Sep. 5, 2023

(54) SYSTEM AND METHOD FOR A TRACHEOSTOMY TUBE WITH A SECONDARY AIRFLOW OPENING AND A DUAL CUFF ASSEMBLY

(71) Applicant: Kevin Chong Kim, Holmdel, NJ (US)

(72) Inventor: Kevin Chong Kim, Holmdel, NJ (US)

(*) Notice: Subject to any disclaimer, the term of this patent is extended or adjusted under 35 U.S.C. 154(b) by 0 days.

(21) Appl. No.: 17/902,691

(22) Filed: Sep. 2, 2022

Related U.S. Application Data

(63) Continuation-in-part of application No. 17/848,273, filed on Jun. 23, 2022.

(51) Int. Cl.
*A61M 16/04* (2006.01)
*A61M 25/00* (2006.01)

(52) U.S. Cl.
CPC ...... *A61M 16/047* (2013.01); *A61M 16/0434* (2013.01); *A61M 16/0475* (2014.02); *A61M 25/0043* (2013.01); *A61M 2205/0216* (2013.01); *A61M 2205/3331* (2013.01)

(58) Field of Classification Search
CPC .......... A61M 16/0465; A61M 16/0468; A61M 16/047; A61M 16/0472; A61M 16/0475; A61M 16/0477; A61M 16/0484; A61M 16/044; A61M 16/0436; A61M 16/0443; A61M 16/0434; A61M 16/0454; A61M 16/0456; A61M 16/0459; A61M 16/0486; A61M 16/0463; A61M 16/0003; A61M 16/0427; A61M 2016/0027
See application file for complete search history.

(56) References Cited

U.S. PATENT DOCUMENTS

| | | | |
|---|---|---|---|
| 3,481,339 A | 12/1969 | Puig | |
| 5,339,809 A * | 8/1994 | Beck, Jr. | A61M 16/0465 128/207.29 |
| 9,132,212 B2 | 12/2015 | Clayton | |
| 10,369,312 B2 | 8/2019 | Pendleton et al. | |
| 2003/0041863 A1 | 3/2003 | Hargis | |

(Continued)

FOREIGN PATENT DOCUMENTS

| | | | |
|---|---|---|---|
| DE | 202020101607 U1 * | 5/2020 | ........ A61M 16/0465 |
| EP | 2077865 B1 | 7/2009 | |

(Continued)

OTHER PUBLICATIONS

Machine English Translation of DE-202020101607-U1 provided by Espacenet (Year: 2020).*

(Continued)

*Primary Examiner* — Joseph D. Boecker
*Assistant Examiner* — Brian T Khong
(74) *Attorney, Agent, or Firm* — LOZA & LOZA, LLP; Jessica W. Smith

(57) ABSTRACT

A cuff assembly for a tracheostomy tube includes an outer bladder and an inner cuff. The inner cuff is positioned adjacent to the tracheostomy tube, and the outer bladder is positioned adjacent to the inner cuff. The outer bladder is made with a less elastic material and operates at a higher relative pressure. The inner cuff is made with a more elastic or hyper-elastic material and operates at a lower relative pressure. A secondary airflow opening is formed on a lateral wall of the tracheostomy tube between the cuff assembly and a main distal opening of the tracheostomy tube.

25 Claims, 13 Drawing Sheets

(56) References Cited

U.S. PATENT DOCUMENTS

| | | | |
|---|---|---|---|
| 2008/0078403 A1* | 4/2008 | Clayton | A61M 16/04 128/207.15 |
| 2010/0288289 A1* | 11/2010 | Nasir | A61M 16/0493 128/207.14 |
| 2012/0279500 A1* | 11/2012 | Singvogel | A61M 16/04 128/204.18 |
| 2015/0367093 A1 | 12/2015 | Clayton | |
| 2021/0402120 A1 | 12/2021 | Tupper et al. | |
| 2022/0080141 A1 | 3/2022 | Göbel | |

FOREIGN PATENT DOCUMENTS

| | | | | |
|---|---|---|---|---|
| WO | WO-9966975 A1 * | 12/1999 | | A61M 16/04 |
| WO | 2011127407 A1 | 10/2011 | | |
| WO | WO-2016209192 A2 * | 12/2016 | | |

OTHER PUBLICATIONS

PCT/U2023/012533. International Search Report & Written Opinion dated May 10, 2023.

* cited by examiner

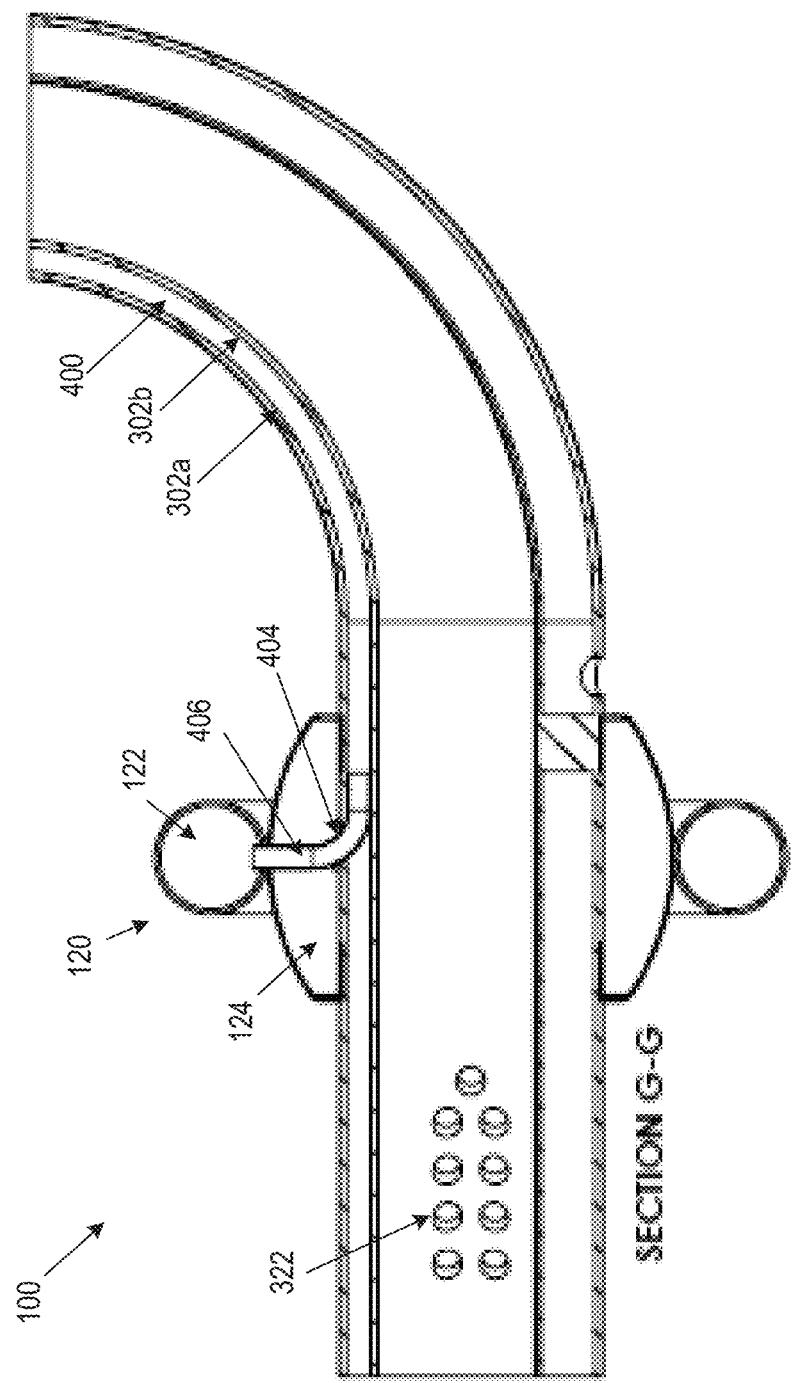

SYSTEM AND METHOD FOR A TRACHEOSTOMY TUBE WITH A SECONDARY AIRFLOW OPENING AND A DUAL CUFF ASSEMBLY

CROSS REFERENCE TO RELATED APPLICATIONS

The present application claims priority under 35 U.S.C. § 120 as a continuation-in-part application to U.S. patent application Ser. No. 17/848,273 entitled, "SYSTEM AND METHOD FOR AN ENDOTRACHEAL TUBE CUFF ASSEMBLY," filed Jun. 23, 2022, and hereby expressly incorporated by reference herein.

FIELD

This application relates to systems and methods for a cuff assembly implemented in a medical device and more particularly, a tracheostomy tube with a secondary airflow opening, a cuff assembly and a secretion collection and clearance system.

BACKGROUND

A tracheostomy tube is a generally L-shaped tube including a flange, outer cannula, inner cannula, and cuff. The outer cannula is divided into proximal, curved, and distal segments. The proximal and distal segments of the tracheostomy tube are relatively straight and connected through the middle, curved segment. The distal and curved segments are surgically inserted into a patient through a tracheostomy stoma (a hole made in the neck and windpipe), with a placement of the distal segment along the longitudinal axis of the trachea. The proximal segment, oriented at almost 90 degrees from the distal segment, protrudes from the tracheostomy stoma. The flange extends from the sides of the proximal segment to stabilize the tracheostomy tube outside of the tracheostomy stoma. The flange includes slits or holes on opposing ends to attach cloth ties or a strap that wraps around the neck. An inner cannula fits internally to the outer cannula and may be removed or replaced to maintain the cleanliness of the tracheostomy tube.

An inflatable cuff is disposed on the distal segment of the tracheostomy tube and lies within the trachea. An inflation tube connects to a pilot balloon and one-way inflation valve for inflation of the cuff. In known tracheostomy tubes, the inflatable cuff occupies almost a total length of the distal segment and helps to prevent leakage of fluids into the lungs of a patient.

The tracheostomy tube is then coupled to a ventilator and provides a conduit for the patient to breathe when the patient has an airway narrowing or obstruction proximal to the trachea (upper airway). This upper airway blockage may occur with an infection, tumor, trauma, or hemorrhage. For the patient with acute airway obstruction, a tracheostomy tube becomes lifesaving. However, should the tracheostomy tube occlude, the patient has no alternative means to breathe, and so the occlusion may prove fatal. Unfortunately, obstructions of the main tracheostomy tube opening occur not infrequently. Obstructions most commonly are caused by thick secretions, mucous plugs, blood clots, foreign body, or kinking or dislodgement of the tube. Tracheostomy tubes currently have a system for removal of such secretions but this system is not ideal and often fails to prevent occlusions.

In addition, a principal goal of the inflatable cuff is to provide a maximum airway seal and cause minimal damage to the airway. Though this goal seems simple and straightforward, successfully achieving this goals has been elusive. This failure continues despite the diverse modifications and advances that have been made vis-a-vis materials, shape, and volumetric structure.

In view of the above disadvantages described in this specification, there is a need for an improved tracheostomy tube providing a means for a patient to breath in the event that the main tracheostomy tube opening becomes occluded. Furthermore, there is a need for an improved system and method for secretion collection and removal to help prevent occlusions in the tracheostomy tube. Still furthermore, there is a need for an improved cuff system that helps to reduce micro-aspiration and infection of the lungs by maintaining a good seal with the tracheal wall but without unduly harming the tracheal wall.

SUMMARY

In one aspect, a tracheostomy tube comprises an outer cannula having a distal segment, wherein the distal segment includes the main distal opening. The tracheostomy tube also includes a cuff assembly at the distal segment of the tracheostomy tube. The cuff assembly includes an inflatable inner cuff with an inner surface and an outer surface, wherein the inner surface is positioned adjacent to the outer cannula; and an inflatable outer bladder positioned adjacent to the outer surface of the inner cuff. The inner cuff has a first elasticity and the outer bladder has a second elasticity that is less than the first elasticity of the inner cuff. The distal segment further forms a secondary airflow opening between the cuff assembly and the main distal opening.

In another aspect, a tracheostomy tube comprises a cuff assembly including an inflatable inner cuff with an inner surface and an outer surface, wherein the inner cuff is configured for a first pressure range and an inflatable outer bladder positioned adjacent to the outer surface of the inner cuff, wherein the outer bladder is configured for a second pressure range, wherein the first pressure range of the inner cuff is less than the second pressure range of the outer bladder. The tracheostomy tube includes an outer cannula having a distal main opening, wherein an inner surface of the cuff assembly is positioned adjacent to the outer cannula and wherein the outer cannula forms a secondary airflow opening between the cuff assembly and the main distal opening.

In one or more of the above aspects, the secondary airflow opening comprises a plurality of openings formed on the lateral wall of the distal segment between the cuff assembly and the main distal opening.

In one or more of the above aspects, the plurality of openings each have slanted walls, wherein an interior opening of each of the plurality of openings is more distal than an exterior opening of each of the plurality of openings.

In one or more of the above aspects, an inner cannula is positioned internally to the outer cannula and the secondary airflow opening formed in the outer cannula comprises at least one opening that substantially exposes the plurality of openings formed in the inner cannula.

In one or more of the above aspects, the secondary airflow opening formed in the outer cannula comprises a first plurality of openings formed in the outer cannula that substantially align with a second plurality of openings formed in the inner cannula.

BRIEF DESCRIPTION OF THE DRAWINGS

FIG. 4 illustrates a cross-sectional view of an exemplary embodiment of the tracheostomy tube.

DETAILED DESCRIPTION

The word "exemplary" or "embodiment" is used herein to mean "serving as an example, instance, or illustration." Any implementation or aspect described herein as "exemplary" or as an "embodiment" is not necessarily to be construed as preferred or advantageous over other aspects of the disclosure. Likewise, the term "aspects" does not require that all aspects of the disclosure include the discussed feature, advantage, or mode of operation.

Embodiments will now be described in detail with reference to the accompanying drawings. In the following description, numerous specific details are set forth in order to provide a thorough understanding of the aspects described herein. It will be apparent, however, to one skilled in the art, that these and other aspects may be practiced without some or all of these specific details. In addition, well known steps in a method of a process may be omitted from flow diagrams presented herein in order not to obscure the aspects of the disclosure. Similarly, well known components in a device may be omitted from figures and descriptions thereof presented herein in order not to obscure the aspects of the disclosure.

Embodiment of the Secondary Airflow Opening

Figure 1:
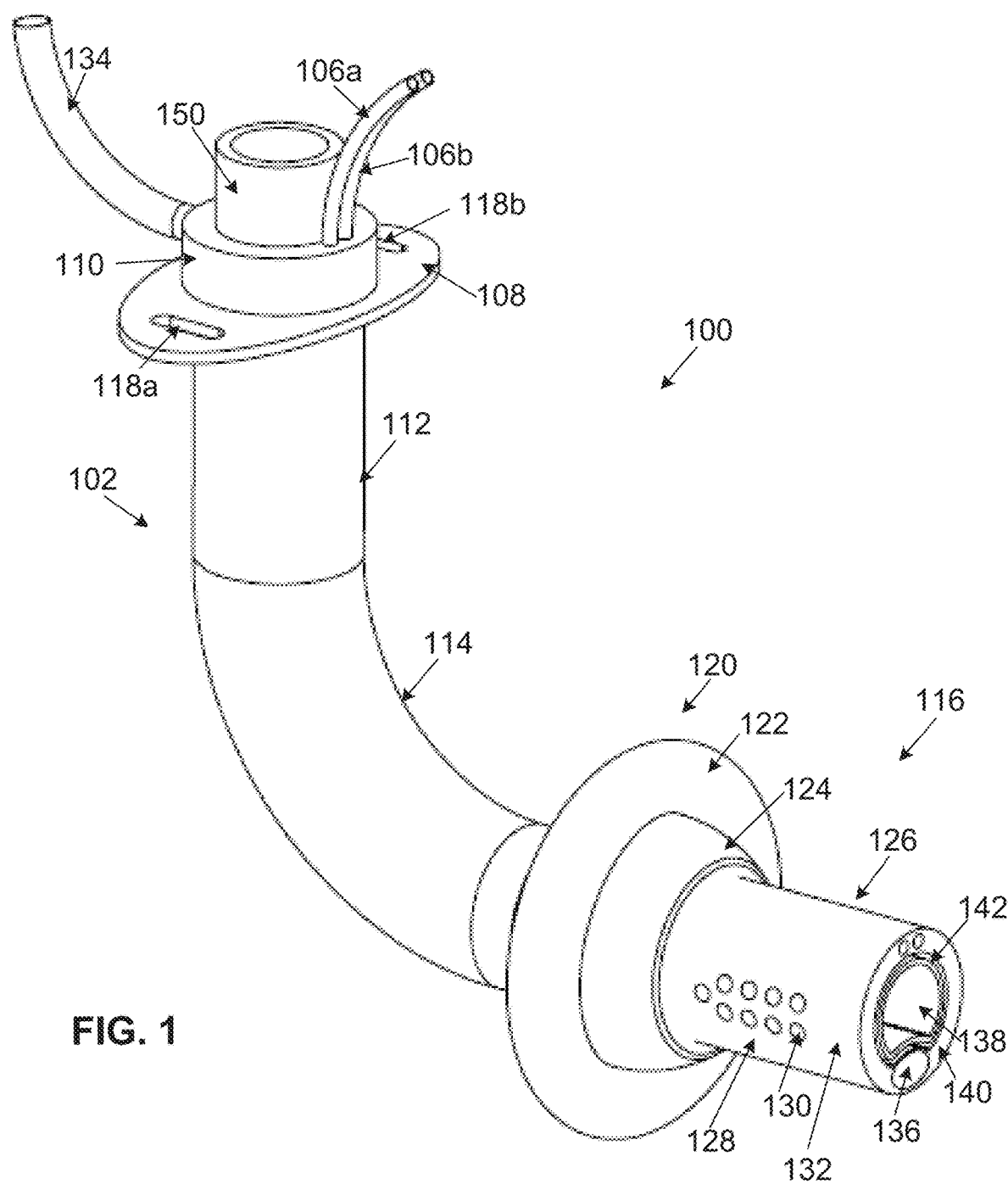
FIG. 1 illustrates an elevational view of an exemplary embodiment of a tracheostomy tube with a secondary airflow opening.

FIG. 1 illustrates an elevational view of an exemplary embodiment of a tracheostomy tube 100 with a secondary airflow opening 128. The tracheostomy tube 100 includes an outer cannula 102 and an inner cannula 150, wherein the inner cannula is positioned internally to the outer cannula. The outer cannula 102 and the inner cannula 150 may comprise a soft polyvinyl chloride (PVC) material.

The outer cannula 102 includes a proximal segment 112, a curved middle segment 114, and a distal segment 116. The proximal segment 112 of the outer cannula 102 includes a flange 108 or plate that circumferentially extends outward from the outer cannula. The flange 108 includes two slits 118a, 118b on opposing sides. A cotton bandage or strap is secured in the slits 118a, 118b of the flange to hold the tracheostomy tube 100 against a neck of a patient. The proximal segment 112 further includes a hub 110 extending outward from the flange 108. The inner cannula 150 is inserted through a proximal opening in the hub 110. The proximal end of the inner cannula 150 then connects to a ventilator.

The outer cannula 102 of the tracheostomy tube 100 includes a curved middle segment 114 and a distal segment 116 configured to fit within a trachea of a patient. The middle segment 114 is curved such that the proximal segment 112 is between at an approximately 80 degree to an approximately 90 degree angle to the distal segment 116. The distal segment 116 includes a cuff assembly 120, a distal end 126, and a main distal opening 138. The main distal opening 138 is the opening at the distal end of the tracheostomy tube 100, e.g. formed by the ending of the tracheostomy tube 100. For example, the main distal opening 138 is formed between the distal bottom surface 140 of the wall 132 of the outer cannula 102 and (if present) the distal bottom surface 142 of the wall of the inner cannula 150.

The cuff assembly 120 includes an inner cuff 124 and outer bladder 122, as described in more detail hereinbelow.

A secondary airflow opening is not possible on currently known tracheostomy tubes due to structural limitations. The main limitation is a lack of necessary space on the distal end 126 between an inflatable cuff and main distal opening 138. A secondary airflow opening must have a total area sufficient to maintain airflow for respiration of a patient in case of occlusion of the main distal opening 138. As described hereinabove, in currently known tracheostomy tubes, the inflatable cuff occupies an almost entire length of the distal segment 116. As such, the distal end 126 has insufficient length from the inflatable cuff to the main distal opening 138 for a secondary airflow opening.

The present specification describes a novel cuff assembly 120 with a length less than typical inflatable cuffs. For example, the length of the cuff assembly $L_{CA}$ is in a range of approximately 10 millimeters (mm) to approximately 20 mm—as opposed to approximately 30 mm on current tracheostomy tubes. Due to the shortened length of this novel cuff assembly 120, an increased length of the distal end 126 is exposed between the cuff assembly 120 and the main distal opening 138. This increased exposed length of the distal end 126 allows for a secondary airflow opening 128. The secondary airflow opening 128 is formed on a lateral (side) wall 132 of the distal segment 116 between the cuff assembly 120 and the main distal opening 138. The secondary airflow opening 128 serves as an alternative conduit for a patient to breathe in the event of occlusion of the tracheostomy tube's main opening 138.

In this embodiment, the secondary airflow opening 128 includes a plurality of fenestrations 130 formed in the wall 132 of the outer cannula 102 and the wall of the inner cannula 150. The fenestrations 130 in the outer cannula 102 must substantially align with the fenestrations in the inner cannula 150. For example, to substantially align, a fenestra 130 in the outer cannula 102 must align with at least approximately 80 percent of its corresponding fenestra in the inner cannula 150. The alignment of the outer cannula 102 and the inner cannula 150 is guided by the suction channel 136 and suction catheter 134, as described in more detail hereinbelow.

In one example, each of the fenestra 130 are between 1 mm to 3 mm in diameter with a total area of the plurality of fenestrations equaling approximately 20 square mm to approximately 80 square mm (depending on the length $L_{DE}$ of the distal end) to provide sufficient airflow. Other size openings and total area of fenestrations 130 may be implemented. The fenestrations 130 are spaced at a distance to preserve a sufficient amount of the material of the outer cannula 102 to ensure its structural integrity. The plurality of fenestrations 130 thus provide a secondary airflow opening 128 for sufficient ventilation when the main distal opening 138 becomes obstructed.

In an embodiment, each of the fenestra 130 have slanted or tilted walls, e.g. the walls are at an angle with respect to a center line of the distal end 126. For example, an interior opening of a fenestra 130 is more distal than the exterior opening. The angle of the fenestra wall may be between 10 to 45 degrees with respect to the center line of the distal end 126. This configuration of the fenestra 130 helps prevent snagging of the tip of the suction catheter on the interior openings of the fenestrations 130.

Embodiment of the Dual Cuff Assembly

The tracheostomy tube 100 includes the novel cuff assembly 120 disposed at the distal segment 116. Currently, there are two main types of cuffs, low volume, high pressure (LVHP) cuffs and high volume, low pressure (HVLP) cuffs. The first type, LVHP cuffs, are made from stiffer, relatively inelastic materials. Due to their inherent stiffness, a greater level of pressure (50 cm H2O to 100 cm H2O) is required to inflate LVHP cuffs. As a result, LVHP cuffs cause an excessively high pressure on the tracheal mucosa, even when inflated to a minimum pressure to create a seal with the tracheal wall. This high pressure causes an unacceptably high incidence of tracheal ischemia and necrosis, e.g., a 5%-20% incidence rate. Despite that, one crucial advantage of LVHP cuffs, when inflated, is the relative absence of folds or wrinkles, resulting in superior tracheal sealing. LVHP cuffs were first employed in the 1960's, but, today, have been widely replaced by HVLP cuffs.

HVLP cuffs are composed of more elastic, compliant materials that inflate at lower pressures. To compensate for the lower pressure characteristics and create a seal against the tracheal wall, the diameter of the HVLP cuffs are generally 1.5-2 times the diameter of the trachea when fully inflated. However, the increased volume of the HVLP cuffs requires a significant amount of cuff material that adds bulkiness to the HVLP cuff making it more difficult to intubate. Moreover, the excess material has a tendency to form wrinkles or folds due to "incomplete inflation." These wrinkles or folds often create paths for orogastric secretions to pass beyond the HVLP cuff, ultimately leading to micro-aspiration and infection of the lungs.

In examining the effect of cuff pressure on the trachea, it is important to keep in mind that the tracheal wall mucosa capillary perfusion pressure in humans ranges from 22 to 32 mmHg, and tracheal mucosal blood flow may be compromised at applied pressures above 30 cm H2O (22 mmHg), with total occlusion of flow to certain parts at 50 cm H2O (37 mmHg). It is apparent, then, that there is only a small overlap between the safety pressure range and that of complication. The window of efficacy and safety, indeed, is very narrow, if nonexistent.

The required pressure for typical HVLP cuffs to achieve a reasonable inflation with an acceptable number of folds or wrinkles is about 32 cm H2O. The guidelines established by various medical societies and organizations recommend maintaining the HVLP cuff pressure within a range of 20 cm H2O to 30 cm H2O to avoid occlusion of tracheal mucosal blood flow. Nevertheless, even with a strict adherence to the recommendations, many patients are still placed in harms' way. In fact, a study has shown that about 10% of patients on mechanical ventilation develop ventilator-associated pneumonia (VAP), and the mortality rate in VAP is estimated at 13%. In addition, patients with VAP face a longer hospital course and incur higher healthcare costs than similarly ill patients without VAP. Given that in the U.S., there are approximately 750,000 patients annually that require ventilation, the human and financial tolls of VAP is enormous.

Unfortunately, studies have shown that even at pressures up to 60 cm H2O, micro-aspiration still occurs with HVLP cuffs, suggesting the continued presence of cuff wrinkles, allowing the passage of secretions, even at higher pressures. So, even though HVLP cuffs appear superior because they are capable of producing a seal at a lower pressure level and avoiding necrosis of the tracheal wall, they are still far from being ideal.

Referring back to FIG. 1, the cuff assembly 120 is now described in more detail. Unlike previously known cuffs, the cuff system 120 comprises at least two separately controlled inflating bladders. The cuff assembly 120 includes a first inner cuff 124 positioned around and adjacent to the outer cannula 102 that is configured to inflate radially outwards from the tracheostomy tube 100. A second, torus-shaped outer bladder 122 is positioned around and adjacent to the inner cuff 124 wherein at least a portion of the inner cuff 124 lays between the outer bladder 122 and the tracheostomy tube 100. The outer bladder 122 is configured to inflate radially outward from the inner cuff 124 such that an outer surface of the outer bladder 122 contacts the tracheal wall.

The inner cuff 124 and the outer bladder 122 may be a cylindrical or toroidal shape. For example, as seen in FIG. 1, the outer bladder 122 is a torus shaped ring with a circular cross section when inflated. The inner cuff 124 has a cylindrical shape with an arched outer surface that forms a ring around the tracheostomy tube 100. In this example, the length of the inner cuff is in the range of 10 mm to 20 mm, and the length of the outer cuff is in the range of 5 mm to 9 mm. The outer bladder 122 is bonded to the inner cuff 124 and not tethered to the outer cannula 102 of the tracheostomy tube 100. The inner cuff 124 is attached to the outer cannula 102 by an adhesive and/or a band.

The inner cuff 124 and the outer bladder 124 have separate inflation means. For example, a first inflation tube 106a is positioned within a first channel of the outer cannula 102 and includes a distal end coupled to the inner cuff 124. A proximal end of the first inflation tube 106a extends from the hub 110 and connects to a pilot balloon and one-way inflation valve for inflation of the inner cuff 124. A separate, second inflation tube 106b is positioned within a second channel of the outer cannula 102 and includes a distal end coupled to the outer bladder 122. A proximal end of the second inflation tube 106b extends from the hub 110 and connects to a pilot balloon and one-way inflation valve for inflation of the outer bladder 122.

Due to the separate inflation tubes 106a-b, the outer bladder 122 and inner cuff 124 may be inflated to and maintained at different pressures. In an embodiment, the inner cuff 124 is a low-pressure inflatable cuff and is configured to function at a low pressure range of 10 cm H2O to 20 cm H2O. In contrast, the outer inflating bladder 122 is configured to inflate to a higher pressure range of 50 cm H2O to 150 cm H2O. The inner cuff 124 thus operates in a pressure range that is less than the pressure range of the outer bladder 122.

In addition, the inner cuff 124 comprises a relatively elastic material while the outer bladder 122 comprises a relatively inelastic material, e.g., the material of the outer bladder 122 is less elastic than the material of the inner cuff 124. For example, the relatively elastic material of the inner cuff 124 may include one or more of: rubber, silicone, latex, polyvinyl chloride (PVC), neoprene, polyisoprene, or polyurethane (PU). The relatively inelastic material of the outer bladder 122 may include one or more of: polyethylene teraphthalate (PETP), low-density polyethylene (LDPE), polyvinyl chloride (PVC), silicone, neoprene, polyisoprene, or polyurethane (PU).

In use, e.g., when inserted into a trachea and then pressurized to an inflated state, the first, inner cuff 124 behaves as a HVLP type cuff while the second, outer bladder 122 behaves as a LVHP type cuff. The more compliant inner cuff 124 is able to temper the pressure applied on the tracheal wall (the "tracheal pressure") by the higher pressurized outer bladder 122. In other words, the lower pressure, more elastic inner cuff 124 is configured to absorb excessive pressure that may otherwise be exerted on the tracheal wall by the outer bladder 122. For example, since the inner cuff 124 is more compliant and elastic, the cuff assembly 120 applies a lower total pressure/force against the tracheal wall, e.g., lower than the outer bladder pressure. The force of the inner cuff 124 acts radially on the outer bladder 122 and thus represents the force ultimately exerted on the trachea as the tracheal pressure. So, the radial force produced by the inner cuff 124 and acted upon the outer bladder 122, then, is the tracheal pressure. For example, when the outer bladder pressure is greater than that of the inner cuff pressure, and the outer bladder is inflated so that the outer surface touches the trachea, the intercuff pressure is the same as the tracheal pressure.

In addition, due to its operation at a high pressure, the outer bladder 122 in an inflated state forms a relatively smooth surface with fewer folds or wrinkles, e.g. than a LVHP cuff. This reduction in wrinkles reduces the risk for leakage and creates a more uniform tracheal seal.

In this way, the cuff assembly 120 utilizes an innovative system to titrate the tracheal pressure thereby reducing tracheal complications. By incorporating the characteristics of HVLP and LVHP cuffs into one system, the cuff system 120 exploits the advantages found in both types of cuffs: superior tracheal seal and greater safety to the trachea. The cuff system 120 features the advantages of superior seal against the tracheal wall with reduced tracheal damage. The cuff assembly 120 thus helps protect the lungs from being contaminated with orogastric contents or blood without undue harm to the tracheal wall.

In an embodiment, the tracheostomy tube 100 also includes a secretion removal system implemented to remove secretions, aspirations or other fluids that may accumulate around a proximal side of the cuff assembly 120. A suction channel 136 is formed within the posterior aspect of the outer cannula 102 and extends from the hub 110 to a point just proximal to the inner cuff 122 where it forms an opening. In one example, the inner cannula 150 has a cylindrical L-shape with a posterior external wall indentation configured to form an upper portion of the suction channel 136, as shown and described in more detail with respect to FIG. 5A. The outer cannula 102 has a cylindrical L-shape with a posterior internal wall indentation configured to form a lower portion of the suction channel 136.

Figure 3:
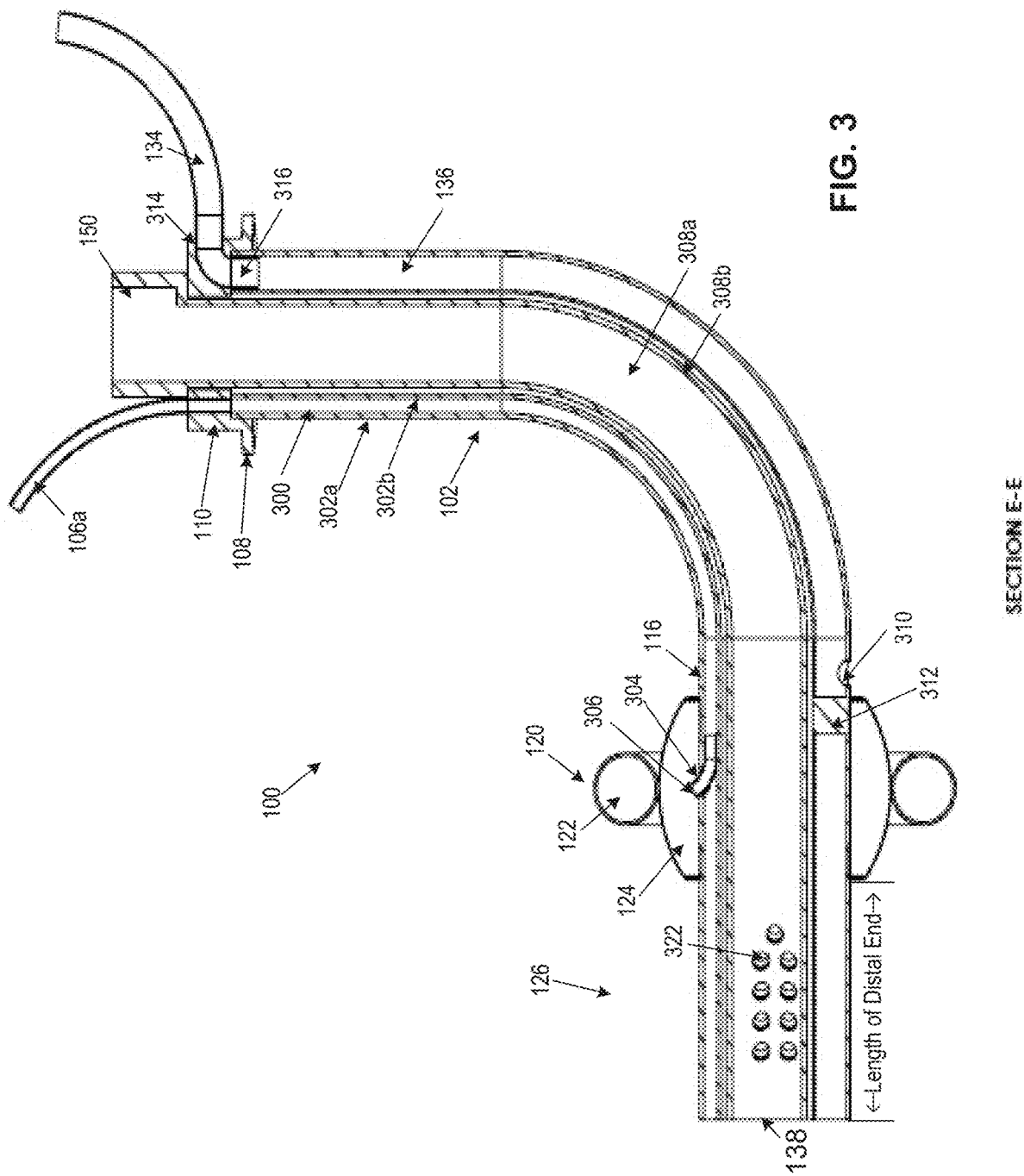
FIG. 3 illustrates a cross-sectional view of an exemplary embodiment of the tracheostomy tube.

An opening is formed in the outer wall of the cannula 102 that fluidly connects the suction channel 136 to the trachea, as shown in more detail with respect to FIG. 3 and FIG. 4. The opening is preferably on a posterior side of the outer cannula 102 at a proximal side of the cuff assembly 120. A suction catheter 134 attaches to a proximal end of the suction channel 136 at the hub 110. A vacuum may then attach to the suction catheter 134 to remove secretions or other fluids that accumulate on the proximal side of the cuff assembly 102. The suction channel 136 is thus implemented within the tracheostomy tube 100. The suction of secretions from the trachea may occur at periodic intervals or continuously using the suction channel 136.

Figure 2:
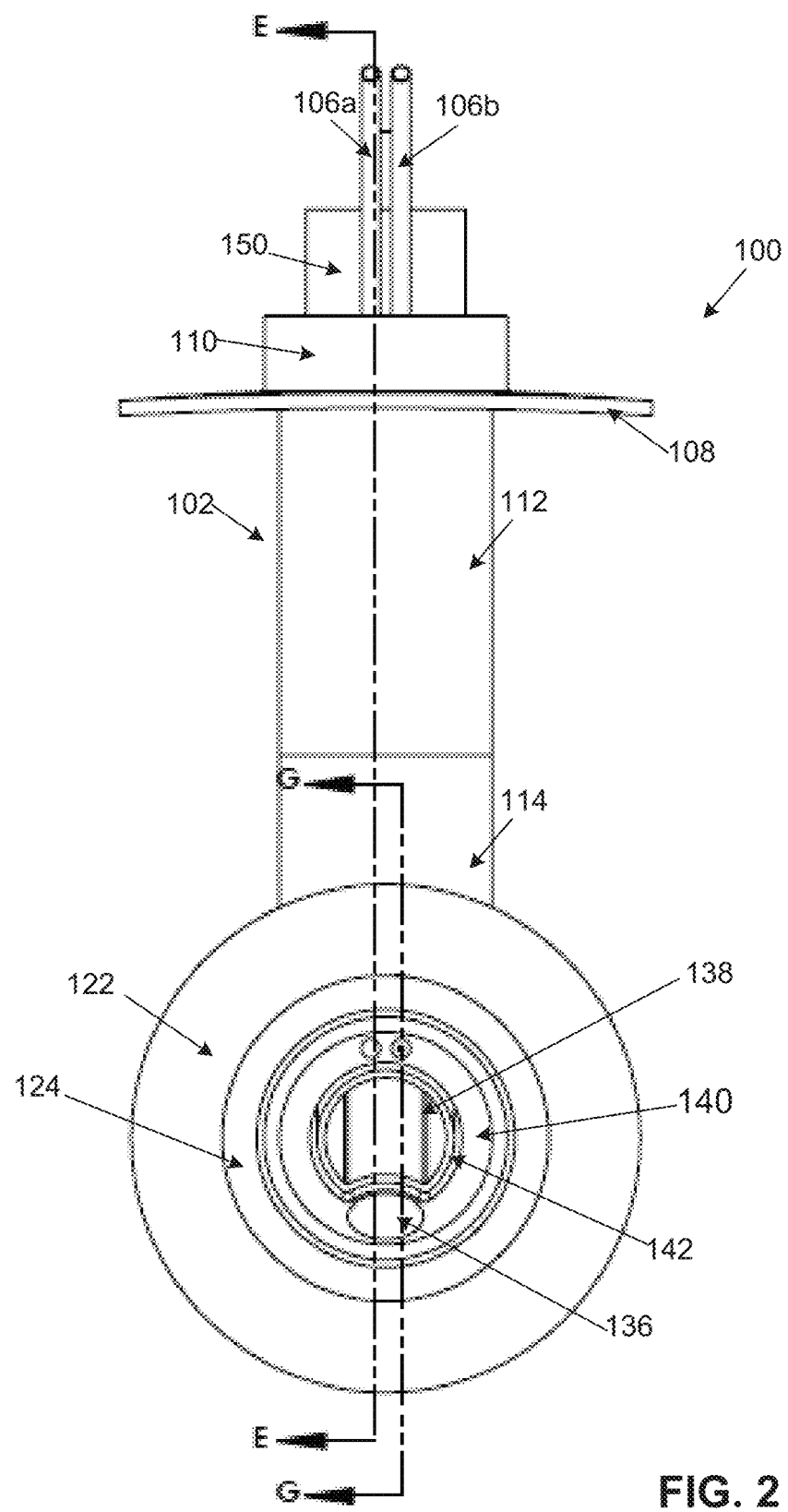
FIG. 2 illustrates a front elevational view of an exemplary embodiment of the tracheostomy tube.

FIG. 2 illustrates a front elevational view of an exemplary embodiment of the tracheostomy tube 100. As seen in this FIG. 2, the outer diameter $D_{OH}$ of the hub 110 is greater than the outer diameter $D_{ODS}$ of the distal segment 112 of the outer cannula 102. The flange 108 extends outward between a distal side of the hub 110 and the distal segment of the outer cannula 102. A cross-section E-E and a cross-section G-G are defined as well.

FIG. 3 illustrates a cross-sectional view of an exemplary embodiment of the tracheostomy tube 100. This cross-sectional view is along cross-section line E-E defined in FIG. 2 and illustrates the first inflation line 106a positioned in a first channel 300. The first channel 300 is formed between an inner wall 302b and an outer wall 302a of the outer cannula 102. The channel 300 extends from a proximal side of the flange, such as at the hub 110, to at least the cuff assembly 102 on an anterior side of the outer cannula 102. A distal end 306 of the inflation tube 106a extends through an opening 304 in the outer wall 302a of the outer cannula 102 into the inner cuff 124. The inflation tube 106a forms an airtight, fluid connection for inflation of the inner cuff 102.

On a posterior side of the tracheostomy tube 100, the suction channel is disposed within the wall of the outer cannula. A proximal end 316 of the suction channel 136 is positioned proximal to the flange 108 and includes an opening for insertion of the suction catheter 134 through a passageway 314 formed in the hub 110. A vacuum or syringe is then coupled to the suction catheter 134 for periodic or continuous evacuation of the suction channel 136.

At a distal end of the suction channel 136, an opening 310 is formed in a posterior outer wall of the outer cannula 102. The opening 310 is positioned proximal to the cuff assembly 120. The opening 310 allows secretions and other fluid that build up around the cuff assembly 120 to flow into the suction channel 136 for evacuation. In another embodiment, e.g. described with respect to FIGS. 7-8, the suction catheter 134 may extend the length of the suction channel 136 and to or through the opening 310.

A stopper 312 is positioned in the channel 136 distally from the opening 310. The stopper 310 seals the suction channel 136 to prevent secretions from flowing to the distal end of the outer cannula 102 and out into the lungs. In another embodiment, the suction channel 136 ends distally from the opening 310. For example, the channel 136 is no longer formed between the outer cannula 102 and the inner cannula 150 and the inner wall 302b of the outer cannula 102 lays adjacent to the outer wall 308b of the inner cannula 150.

The distal end 126 of the tracheostomy tube 100 between the cuff assembly and the main opening 138 has a length $L_{DE}$ of at least 10 mm due to the decreased length of the cuff assembly 126, and the length $L_{DE}$ of the distal end may be 20 mm or more. At a distal end 126, the inner wall 308a of the inner cannula 150 includes a plurality of fenestrations 322 that form a part of the secondary airflow opening 128. The plurality of fenestrations 322 in the inner cannula 150 substantially align with the plurality of fenestrations 130 in the outer cannula 102. For example, the openings for the fenestrations 322 on the outer wall 308b of the inner cannula 150 substantially overlap with the openings for the corresponding fenestrations 130 on the inner wall 302b of the outer cannula 102 when properly aligned. A substantial overlap means at least an 80% overlap in area of the openings.

In an embodiment, each of the fenestra 322 have slanted or tilted walls, e.g. the walls are at an angle with respect to a center line of the distal end 126. For example, an interior opening of a fenestra 130 is more distal than the exterior opening. The angle of the fenestra wall may be between 10 to 45 degrees with respect to the center line of the distal end 126. This configuration permits a smooth introduction of a suction catheter into the inner cannula 150 and helps prevent snagging of the tip of the suction catheter on the interior openings of the fenestrations 130.

Though the secondary airflow opening 128 is shown positioned on a first lateral side of the tracheostomy tube 102, the plurality of fenestrations 322 may be positioned on the opposing lateral side of the tracheostomy tube 102, or on an anterior side of the tracheostomy tube 102. In addition, a second plurality of fenestrations may be positioned on one or more of the second opposing lateral side, an anterior side, or a posterior side. The plurality of fenestrations may be positioned circumferentially around the tracheostomy tube 102 or in other configurations. In addition, the diameter of the fenestrations 322 may be larger or smaller depending on the number of fenestrations 322. The configuration of the fenestrations 322 must include a sufficient diameter of each fenestra and number of fenestra to provide the necessary airflow for respiration.

FIG. 4 illustrates another cross-sectional view of an exemplary embodiment of the tracheostomy tube 100. This cross-sectional view is along cross-section line G-G defined in FIG. 2 and illustrates the second inflation line 106b positioned in a second channel 400. The second channel 400 is formed between an inner wall 302b and an outer wall 302a on an anterior side of the outer cannula 102. The second channel 400 extends from a proximal side of the flange 108 at the hub 110 of the outer cannula 102 to at least the cuff assembly 102. The second inflation line 106b is positioned inside the second channel 400. A distal end 406 of the inflation tube 106b extends through a sealed opening 404 in the outer wall 402b of the outer cannula 102 into the outer bladder 122. The inflation tube 106b thus forms an airtight, fluid connection for inflation of the outer bladder 122.

In this embodiment, there are two channels 300, 400 formed in the anterior wall of the outer cannula 102 for holding the inflation lines 106a, 106b. In another embodiment, the two channels 300, 400 may be formed in a lateral wall of the outer cannula 102. In yet another embodiment, a single channel may hold both the inflation lines 106a, 106b. In yet another embodiment, the channels 300, 400 may be formed between the inner cannula 150 and outer cannula 102, e.g. on the anterior side of the tracheostomy tube 100. Other implementations may also be possible for positioning the inflation lines 106a, 106b from a proximal side of the flange 108 to the cuff assembly 120 of the tracheostomy tube 100.

Figure 5A:
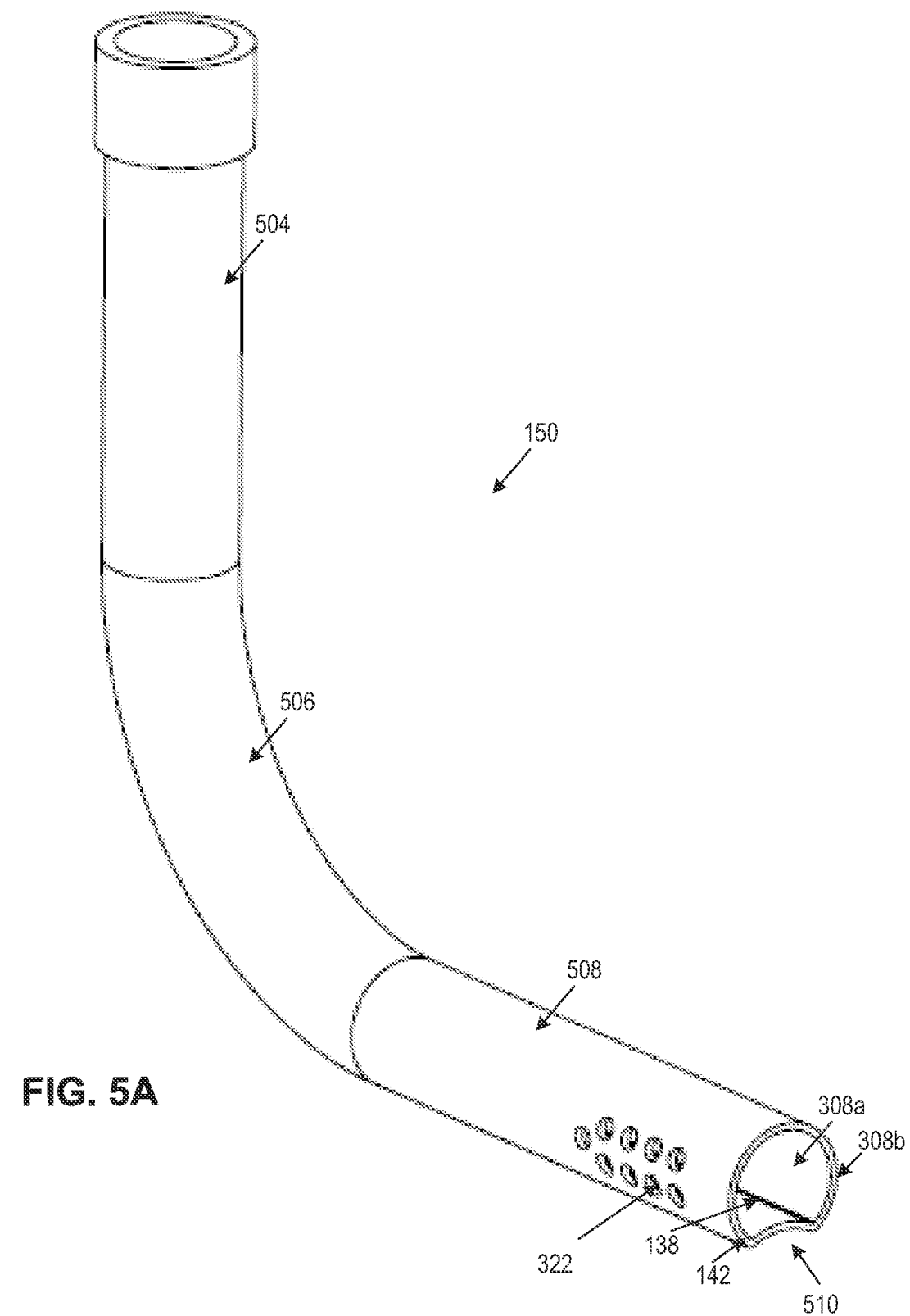
FIG. 5A illustrates an exemplary embodiment of the inner cannula of the tracheostomy tube.

FIG. 5A illustrates an exemplary embodiment of the inner cannula 150 of the tracheostomy tube 100. The inner cannula 150 fits internally to the outer cannula 102 and is removable for replacement and/or cleaning. As with the outer cannula 102, the inner cannula 102 includes a distal segment 508, a proximal segment 504, and a middle segment 506 coupled between the proximal segment 504 and the distal segment 508. The middle segment 506 is curved such that the proximal segment 504 is at an approximately 80 degree to approximately 90 degree angle with respect to the distal segment 508. The distal segment 508 includes the main distal opening 138 of the tracheostomy tube 100.

In this embodiment, the suction channel 136 is formed between within the wall of the outer cannula. The inner cannula 150 includes a posterior external wall indentation 510 configured to form an upper portion of the suction channel 136. The indentation 510 is sized to fit an upper portion of the suction catheter 134.

In an embodiment, each of the fenestra 322 on the inner cannula 102 have slanted or tilted walls, e.g. the walls are at an angle with respect to a center line of the distal segment 508. For example, an opening of a fenestra 322 on the interior wall 308a is more distal than the opening of the fenestra 322 on the exterior wall 308b. The angle of the fenestra wall may be between approximately 10 degrees to approximately 45 degrees with respect to the center line of the distal segment 508. This configuration permits a smooth introduction of a suction catheter into the inner cannula 150 and helps prevent snagging of the tip of the suction catheter on the interior openings of the fenestrations 322.

Figure 5C:
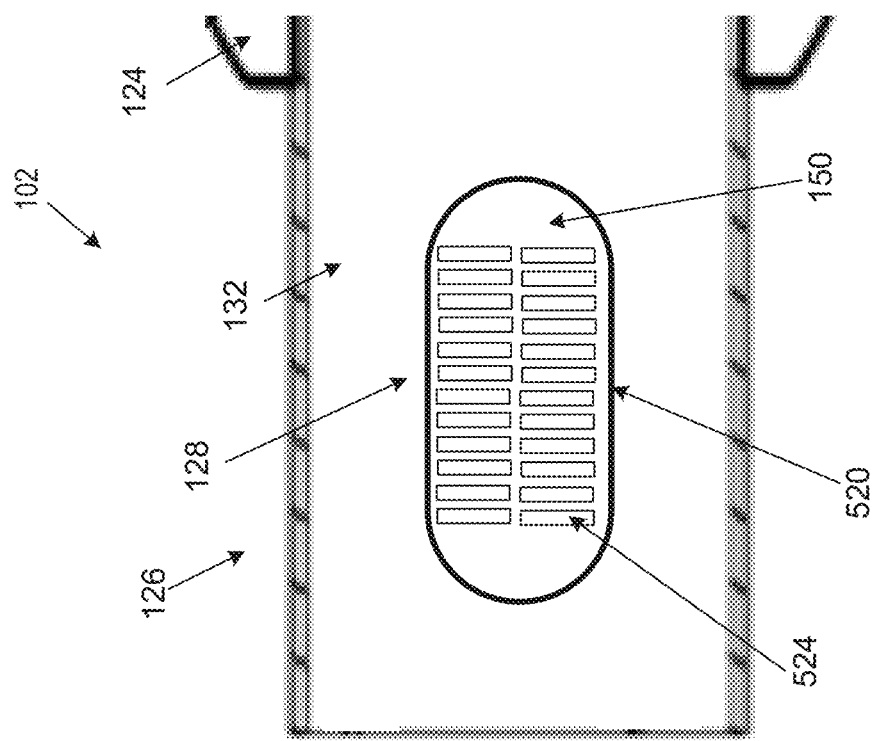
FIG. 5C illustrates a side view of another exemplary embodiment of the secondary airflow opening of the tracheostomy tube.
Figure 5B:
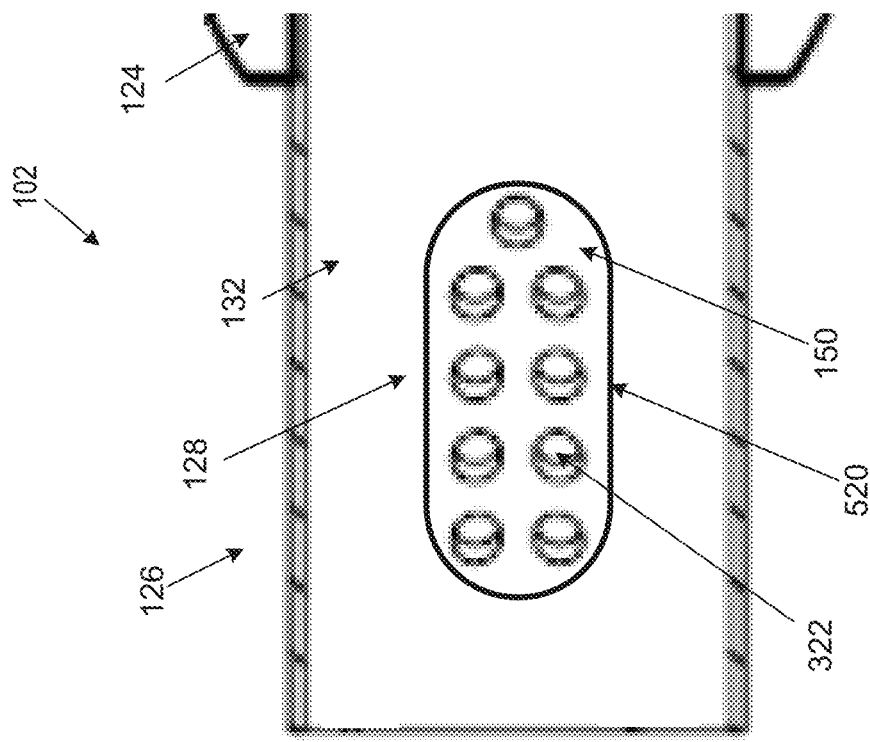
FIG. 5B illustrates a side view of another exemplary embodiment of the secondary airflow opening of the tracheostomy tube.

FIG. 5B illustrates a side view of another exemplary embodiment of the secondary airflow opening 128 of the tracheostomy tube 100. In another embodiment, to obviate the need for alignment of the fenestra, the inner cannula 150 includes the plurality of fenestrations 322 and the outer cannula 102 forms a larger lateral opening 520 that exposes the plurality of fenestrations 130 on the inner cannula 150. The lateral opening 522 substantially covers an area over the plurality of fenestrations 322 on the inner cannula 150. For example, the opening 522 exposes at least 90% of the plurality of fenestrations 322 or at least a total area of approximately 20 square mm to approximately 80 square mm of the fenestrations 322 on the inner cannula 150 to provide sufficient airflow or other area of fenestrations necessary to provide sufficient airflow to the patient.

FIG. 5C illustrates a side view of another exemplary embodiment of the secondary airflow opening 128 of the tracheostomy tube 100. In another embodiment, rather than a plurality of fenestrations, a plurality of slits 524 may be implemented for the secondary airflow opening 128. In this embodiment, the inner cannula 150 forms the plurality of slits 524 and the outer cannula 102 forms the lateral opening 520 that substantially exposes the plurality of slits 524 on the inner cannula 150. The opening 522 substantially covers an area over the plurality of slits 524 on the inner cannula 150. In another embodiment, the outer cannula 102 may also include a plurality of slits that are aligned with the plurality of slits 524 in the inner cannula 150. The plurality of slits 524 may each have slanted or tilted walls. For example, an interior opening of a slit 524 is more distal than an exterior opening of the slit 524.

The secondary airflow opening 128 may thus include a plurality of fenestrations, slits or other shaped openings that are formed in the inner cannula 150 and/or the outer cannula 102. For example, the outer cannula 102 may form a plurality of openings that substantially align with the plurality of openings formed in the inner cannula 102. In another example, the outer cannula 102 may form at least one larger opening that substantially exposes a plurality of openings formed in the inner cannula 102. Other configurations may be implemented such that the area of each opening and the number of openings creates sufficient airflow to the patient.

Second Embodiment of the Cuff System

Figure 6:
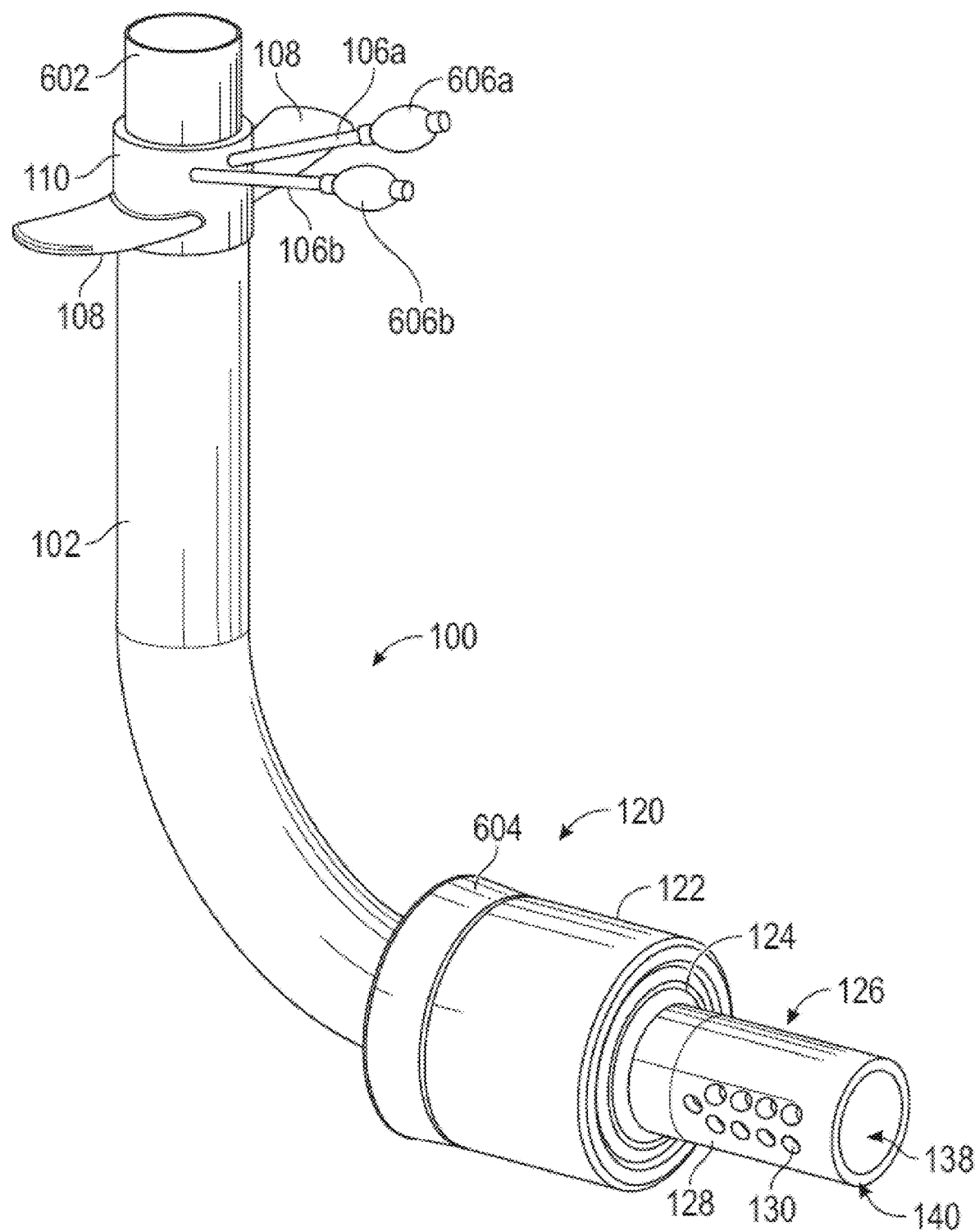
FIG. 6 illustrates a lateral elevational view of another exemplary embodiment of the tracheostomy tube with a second exemplary embodiment of the cuff system.

FIG. 6 illustrates an elevational view of another exemplary embodiment of the tracheostomy tube 100 with a second exemplary embodiment of the cuff system 120. In this embodiment, the tracheostomy tube 100 does not include an inner cannula 150. For example, the inner cannula 150 may be removed or not inserted with the outer cannula 102. In another example, some tracheostomy tubes 100 are not designed to include the inner cannula 150.

At the proximal segment of the tracheostomy tube 100, the flange 108 in this embodiment includes two opposing wings extending from the hub 110. A top portion 602 of the tracheostomy tube 100 attaches to a ventilator. At the distal segment, the main distal opening 138 is formed between the distal bottom surface 140 of the wall 132 of the outer cannula 102. The tracheostomy tube 100 also includes the secondary airflow opening 128 on a lateral side of the outer cannula 102 between the cuff assembly 120 and the main distal opening 138. The secondary airflow opening 128 includes the plurality of fenestrations 130.

Similarly to FIG. 1, the cuff assembly 120 includes an inner cuff 124 and an outer bladder 122. The inner cuff 124 and the outer bladder 122 have a more cylindrical shape and in this example, the inner cuff 124 has a shorter length than the outer bladder 122. For example, the length LOB of the outer bladder 122 is approximately 6 mm, and the length $L_{IC}$ of the inner cuff 124 is approximately 15 mm. The outer bladder 122 includes a top surface 604 that extends proximally further than the inner cuff 124 to form a collection receptacle as shown in further detail hereinbelow.

The first inflation line 106a includes an inflation balloon 606a that attaches to a one way valve for inflation of the inner cuff 124. The second inflation line 106b includes an inflation balloon 606b that attaches to a one way valve for inflation of the outer bladder 122. The outer bladder 122 and inner cuff 124 are thus configured to inflate to and maintain different pressures. The relatively elastic inner cuff is configured to operate in an inflated state at a lower pressure, e.g. in a pressure range of 10 cm H2O to 20 cm H2O. In contrast, the less elastic or relatively inelastic outer bladder is configured to operate in an inflated state at a higher pressure range of 50 cm H2O to 150 cm H2O.

In use, e.g., when inserted into a trachea and then pressurized to an inflated state, the first, inner cuff 124 behaves as a HVLP type cuff while the second, outer bladder 122 behaves as a LVHP type cuff. In addition, the outer bladder 122 in an inflated state forms a relatively smooth surface with fewer folds or wrinkles, e.g. than a LVHP cuff. This reduction in wrinkles reduces the risk for leakage and creates a more uniform tracheal seal. In this way, the cuff assembly 100 utilizes an innovative system to titrate the tracheal pressure thereby reducing tracheal complications.

Embodiment of a Secretion Collection Receptacle

A mechanically ventilated (MV) patient experiences a physiologically altered milieu: reduced ability to clear oral and nasal secretions, diminished tracheobronchial mucociliary clearance, increased accumulation of secretions in the lungs and bronchus, reduced cough reflex, and increased likelihood of gastric reflux. The combined effect of all these factors is to predispose the mechanically ventilated patient to ventilator-associated pneumonia (VAP), an infection of the lungs that develops in patients, typically after 48 hours of being on mechanical ventilation.

An accumulation of secretions above a tracheostomy cuff in MV patients is a normal physiological phenomenon. The sources of secretions are oral cavity, sinuses, and stomach (the "orogastric secretions"). It is known that under normal conditions, the oral cavity and sinuses produce up to 3 liters per day of secretions. Again, that does not include gastric refluxate, which may be significant. While a healthy person is capable of eliminating and/or managing secretions, a ventilated patient cannot. Instead, in a ventilated patient, secretions in the trachea accumulate proximal to the tracheostomy cuff or leak past the tracheostomy cuff and into the trachea and lungs.

The concern with accumulation of secretions above the tracheostomy cuff is that secretions are loaded with microorganisms including bacteria and fungus. Since the secretions are heavily contaminated, they should be kept away from sterile organs of the human body. The lungs are one of those sterile organs. As such, it becomes imperative for the treating physician to prevent secretions from leaking into the patient's lungs.

The tracheostomy cuff can be a powerful aspiration-deterrent mechanism. When inflated, the tracheostomy cuff contacts the tracheal wall circumferentially resulting in a seal to prevent leakage of fluids into the lungs. One strategy to combat VAP is to enhance the occlusive functionality of tracheostomy cuffs, e.g. improve the sealing capability of tracheostomy cuffs, thereby reducing secretions leaking into the lungs, as discussed herein with the cuff assembly 120. While this strategy is helpful, if secretions are allowed to accumulate proximal to the tracheostomy cuff, eventually the sheer pressure of the secretions will likely cause the secretions to leak into the lungs. In addition to an effective tracheal occlusion, therefore, an effective means to clear secretions is also needed.

Current systems to clear secretions include a suction tube at a proximal end of the tracheostomy cuff. However, the configuration of the suction tube opening is known to cause direct injury and suction trauma to the tracheal mucosa. Suction tube opening is configured to render it vulnerable to occlusion by the cuff wall. In addition, due to its small size, the suction tube easily occludes. A larger suction tube may increase bulkiness of the tracheostomy tube significant enough to make the intubation process more difficult. In addition, when the suction tube is integrated into the tracheostomy tube, and the suction tube occludes, it is necessary to change out the entire tracheostomy tube and cuff. As such, there is a need for an improved secretion clearance system.

Figure 7:
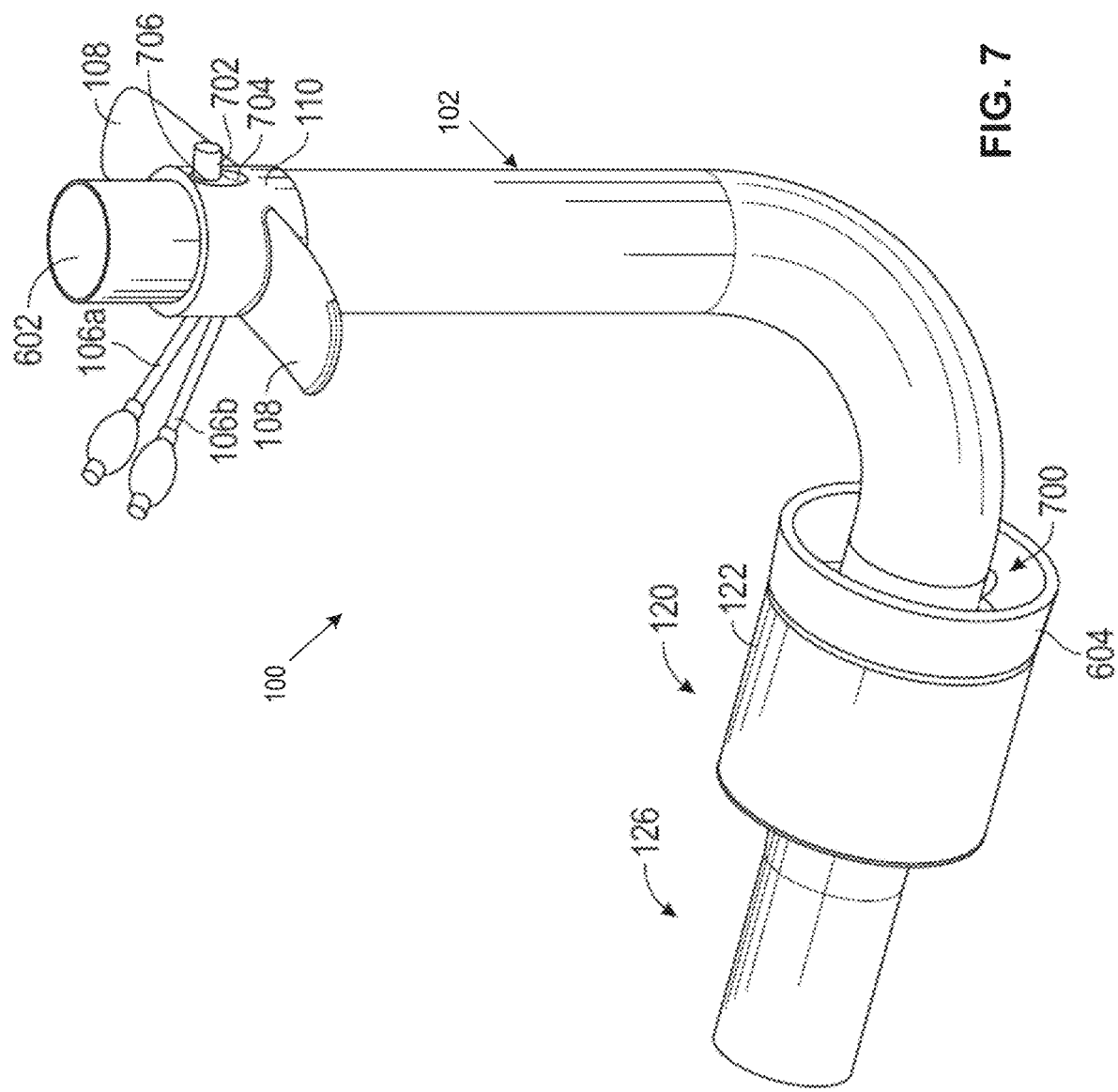
FIG. 7 illustrates another lateral elevational view of an exemplary embodiment of the tracheostomy tube with the second exemplary embodiment of the cuff system.

FIG. 7 illustrates a second lateral elevational view of an exemplary embodiment of the tracheostomy tube 100 with the second exemplary embodiment of the cuff system 120. In this cuff assembly 120, a top surface 604 of the outer bladder 122 extends proximally further than the inner cuff 124 to form a secretion collection receptacle 700. The collection receptacle 700 collects aspirations or other fluids that may accumulate around a proximal end of the cuff assembly 100.

A suction catheter 702 is positioned in a catheter channel 704 that extends from the proximal end of the tracheostomy tube 100 to at least the receptacle 700. The suction catheter 702 is preferably a thin-walled, non-collapsible, and flexible hollow channel or tube. In an embodiment, the suction catheter 702 includes a position indicator 706 that provides an indication of proper positioning of the suction catheter 702 in the catheter channel 704. The position indicator 706 may include markings as a guide or a raised ridge that prevents further insertion of the suction catheter 702 into the catheter channel 704.

The suction catheter 702 is configured to evacuate the collection receptacle 700 through an opening on a posterior side of the tracheostomy tube 102. When a patient is in a prone position, such as typical with intubated patients, secretions will tend to accumulate on a posterior side of the trachea. The suction catheter 702 will thus more likely evacuate accumulated secretions through a posterior opening in the receptacle 700. The proximal end of the suction catheter 702 is configured to connect to a syringe for irrigation or to a vacuum source using suction tubing. When connected, the vacuum source may operate continuously or periodically to clear the secretions in the receptacle 700. An alarm may be triggered when the suction catheter 702 becomes occluded.

In the event of occlusion, the suction catheter 702 may be removed from the catheter channel 704 and replaced with a new suction catheter. The secretion clearance system thus provides an easier method to replace the suction catheter 702 in the event of occlusion that in current methods of replacing the entire tracheostomy tube. The secretion receptacle 700 also helps to protect the tracheal wall from suction trauma or direct injury to the tracheal mucosa from the suction catheter 702. The secretion receptacle 700 also helps to prevent the cuff 120 from being sucked into the catheter 702. Moreover, due to the placement of the catheter channel 704, a larger diameter suction catheter 702 may be employed which reduces the chance of occlusion.

Figure 8:
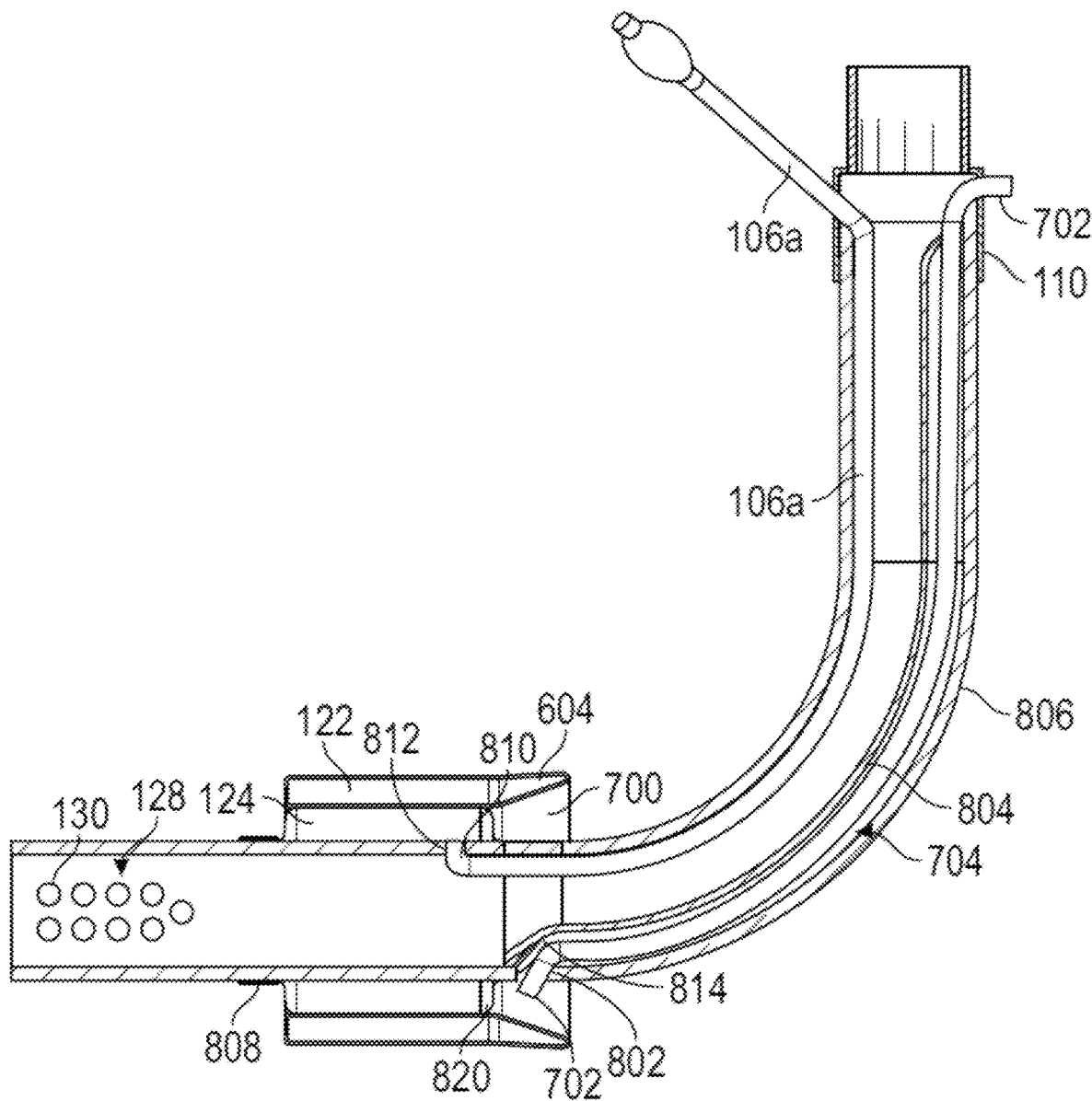
FIG. 8 illustrates a cross-sectional view of an exemplary embodiment of the tracheostomy tube with the second exemplary embodiment of the cuff system.

FIG. 8 illustrates a cross-sectional view of an exemplary embodiment of the tracheostomy tube 100 with the second exemplary embodiment of the cuff system 120. In this cuff assembly 120, the top portion 604 of the outer bladder 122 extends proximally further than the inner cuff 124. The top portion 604 may include an angled, interior surface that slopes toward a proximal surface 820 of the inner cuff 124. The floor of the collection receptacle 700 is defined by the proximal surface 820 of the inner cuff 124 which may be reinforced with a stiffer, less elastic material than other portions of the inner cuff 124. The top surface 820 of the inner cuff and the top portion 604 of the outer bladder thus form the collection receptacle 700.

The catheter channel 704 extends from a proximal end of the tracheostomy tube 100 to at least the collection receptacle 700. The catheter channel 704 is formed by an internal wall 804 positioned within the tracheostomy tube 100 and by the external wall 806 of the tracheostomy tube 100. The catheter channel 704 in this embodiment is positioned on a posterior side of the tracheostomy tube 100 and is configured to fit a suction catheter 702. For example, a suction catheter 702 may have an outer diameter of approximately 4 mm. The suction channel 704 then has an internal diameter greater than 4 mm, such as approximately 4.1 to approximately 4.5 mm, such that the suction catheter 702 is able to slide through the catheter channel 704 during removal and/or insertion.

A posterior opening 802 from the catheter channel 704 to the receptacle 700 is formed in the external wall 806 on a posterior side of the tracheostomy tube 100. A distal end of the suction catheter 702 may extend through the posterior opening 802 into the receptacle 700. The catheter channel 704 may include a slanted surface 814, e.g. formed by the interior wall 804, at the distal end adjacent to the opening 802. The slanted surface 814 helps to guide and position the distal end of the catheter 702 through the opening 802. The suction catheter 702 is thus able to evacuate fluids form the receptacle 700 and help prevent leakage of the fluids into the lungs of a patient.

The inflation line 106a is positioned from a proximal end of the tracheostomy tube 100 to the inner cuff 124. The inflation line 106a may be attached to the interior wall of the tracheostomy tube 100 using an adhesive or other means or be positioned within a designated channel. An opening 812 is formed in the exterior wall 806 of the tracheostomy tube 100 for a distal end 810 of the inflation line 106a to access the inner cuff 124. A similar configuration may be implemented for the inflation line 106b to access the outer bladder 122.

Figure 9A:
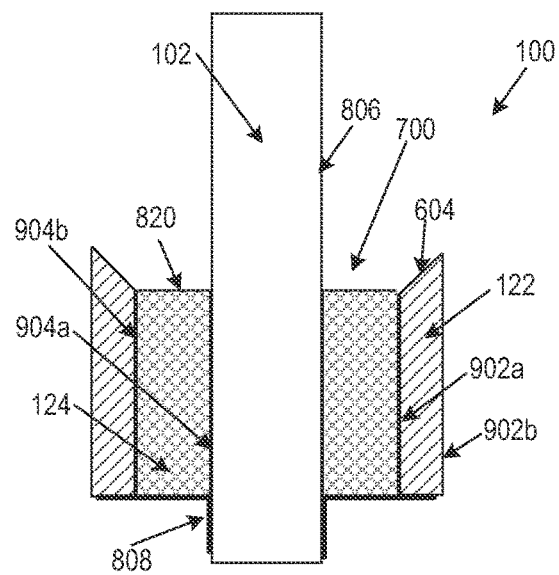
FIGS. 9A, 9B and 9C illustrate block diagrams of cross-sectional views of embodiments of the cuff system.
Figure 9B:
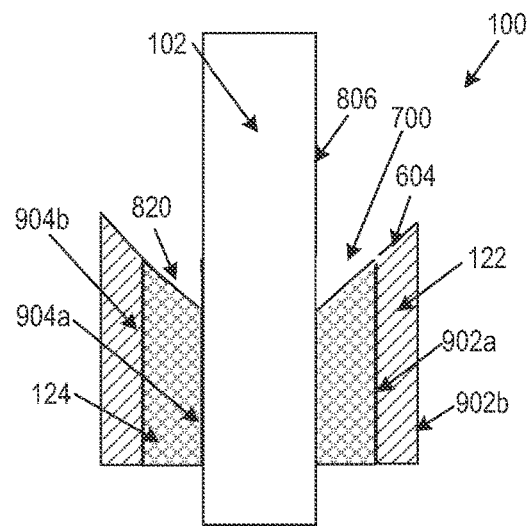
Figure 9C:
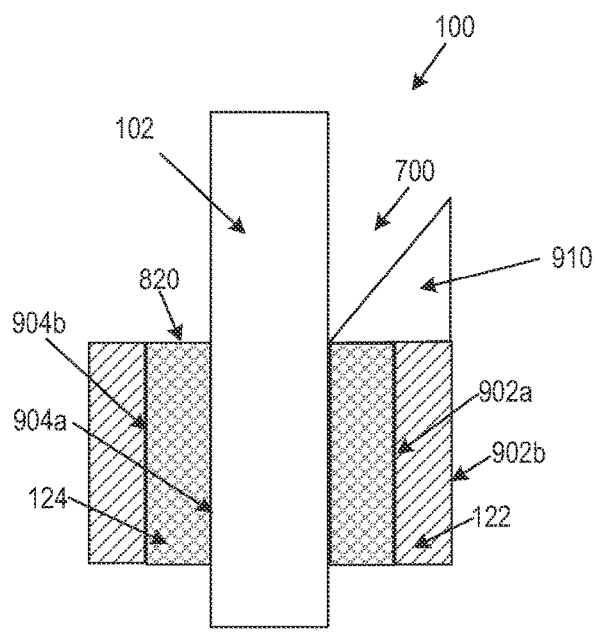

FIGS. 9A-C illustrate block diagrams of cross-sectional views of embodiments of the cuff system 120. Referring to FIG. 9A, it illustrates the cuff system 120 including the inner cuff 124 and outer bladder 122. The outer bladder 122 is a self-contained structure, e.g. it has separate walls from the inner cuff 124. The outer bladder 122 includes an inner surface 902a and outer surface 902b. The inner surface 902a of the outer bladder 122 is positioned adjacent to an outer surface 904b of the inner cuff 124 and may be attached to the outer surface 904b of the inner cuff 124 using, e.g., one or more of adhesives, heat or by other means. The inner surface 904a of the inner cuff 124 is adjacent to and attached to the outer cannula 102 of the tracheostomy tube 100. The inner surface 902a of the outer bladder 122 is proximate to and/or attached to the outer surface 904b of the inner cuff 124, e.g. using adhesives or heat or other means. In addition or alternately, a band 808 may attach to the tracheostomy tube 102 and extend to at least the inner cuff 124. The band 808 may also attach to the outer bladder 122.

In this embodiment of the cuff assembly 120, the length LOB of the outer bladder 122 and the length $L_{IC}$ of the inner cuff 124 are approximately equal. For example, when inflated, the length $L_{IC}$ of the inner cuff 124 is approximately 15 mm, and the length LOB of the outer bladder 122 (without the top portion 604) is approximately 15 mm. In another embodiment, the length LOB of the outer bladder 122 and the length $L_{IC}$ of the inner cuff 124 may be different. For example, the length LOB of the outer bladder (with the top portion 604) may be approximately 15 mm and the length $L_{IC}$ of the inner cuff 124 is approximately 6 mm. In addition, in an embodiment, the width of the outer bladder $W_{OB}$ and the width of the inner cuff $W_{IC}$ are approximately equal. For example, the width of the outer bladder $W_{OB}$ and the width of the inner cuff $W_{IC}$ are approximately 6 mm. In other embodiments, the width of the outer bladder $W_{OB}$ or the width of the inner cuff $W_{IC}$ may be different, e.g. the inner cuff 124 may be wider or less wide than the outer bladder 122. The inner cuff 124 and the outer bladder 122 may have a thickness of approximately 0.00086 inches (0.022 mm) or less. These dimensions are exemplary, and the cuff assembly 120 may be implemented with other dimensions.

To form the collection receptacle 700, a top portion 604 of the outer bladder 122 extends proximally from the inner cuff 124 and is angled inwardly to form a trough. The length of the top portion 604 from the proximal surface 820 of the inner cuff 124 may range between approximately 2 mm to approximately 15 mm. The receptacle 700 may span approximately 90 degrees to approximately 180 degrees on the posterior side of the cuff assembly 120 or span 360 degrees around the circumference of the tracheostomy tube 100. The top portion 604 attaches to the proximal surface 820 of the inner cuff 124 and/or with the tracheostomy tube 100. This prevents leakage between the inner cuff 124 and the outer bladder 122. The top portion 604 of the outer cuff 122 may comprise a rigid PVC sheet to oppose and seal the tracheal wall and allow the secretion to flow into the well. The rigid PVC sheet helps to prevent leakage of the secretion as well.

Alternatively or additionally, the inner cuff 124 may be attached to form a seal against leakage or pressed against the outer bladder 122, e.g. such that secretions or other matter may not leak through the junction. For example, the inner cuff 124 and outer bladder 122 may be adhesively attached or attached using a heating process or a combination thereof that forms a seal to prevent leakage.

In addition, the inner surface 904a of the inner cuff 124 is sealed or attached to or pressed against the outer wall 806 of the tracheostomy tube 100 to prevent leakage. For example, the inner cuff 124 and tracheostomy tube 100 may be adhesively attached or attached using a heating process or a combination thereof. These seal or attachment prevents the leakage of secretions between the tracheostomy tube 100 and the inner cuff 124.

FIG. 9C illustrates another embodiment of the cuff system 120 in which a separate structure 910 attaches to the tracheostomy tube to form the secretion collection receptacle 700. The structure 910 is positioned proximal to the cuff assembly 120 and is attached to the tracheostomy tube 100. Alternately or additionally, the structure 920 may attach to a top proximal surface of the inner cuff 102 and/or a top proximal surface of the outer bladder.

The configurations shown in FIGS. 9A-C are exemplary and other configurations for forming a collection receptacle 700 may be implemented.

Embodiments of the Pressure Regulation System

The benefit and risks of the tracheostomy tube, more than the tube itself, depends on maintaining a predetermined pressure range in the cuff assembly 120. For example, overinflation of the cuff assembly 120 may result in tracheal mucosal injury by causing ischemic damage and vocal cord nerve injury. The damage is due to the constant pressure exerted by the cuff that prevents blood flow to the mucosa of the trachea. This loss of blood may lead tissue necrosis. In addition, damage may also arise due to the repeated abrasion from the cuff moving against the tracheal wall. When the cuff assembly 120 is underinflated and the tracheal seal is inadequate, the patient may not receive sufficient oxygen. Further, the patient is subjected to increased possibility of pneumonia from the aspiration of orogastric content. Thus, maintenance of the pressure of the cuff assembly 120 for a tracheostomy tube 100 is a critical component of patient care, vis-a-vis reduction of tracheal injury and prevention of ventilator-associated pneumonia (VAP).

Currently, several types of automated cuff pressure regulators are available. These current devices monitor an intracuff pressure within a single cuff. However, a close examination reveals a major flaw in this approach. The intracuff pressure does not reflect the precise pressure applied to the tracheal wall. Ultimately, it is the tracheal wall pressure that determines both the risks and benefits of the cuff. Thus, there is a need for an improved system and method to monitor and regulate the cuff pressure.

Figure 10:
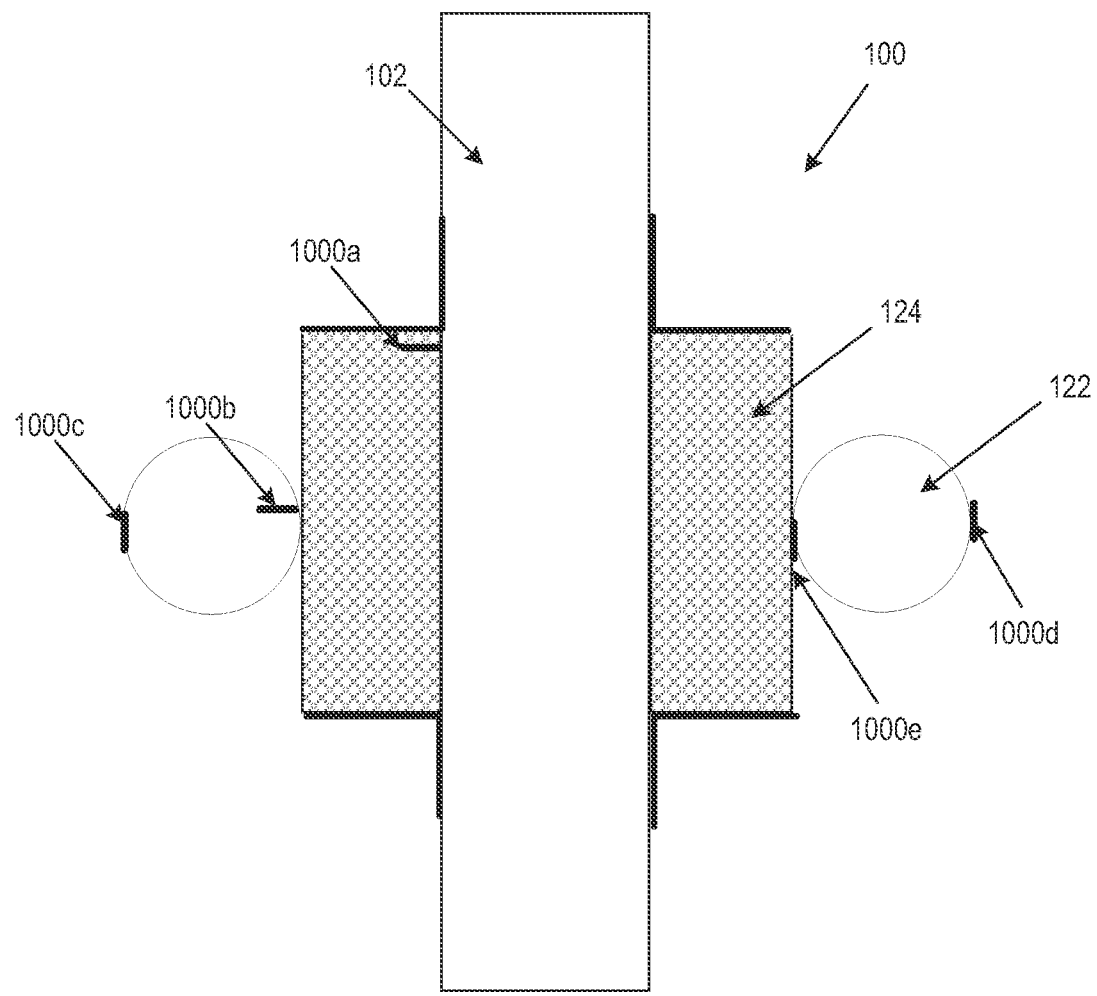
FIG. 10 illustrates a block diagram of an embodiment of the tracheostomy tube with a plurality of pressure sensors.

FIG. 10 illustrates a block diagram of an embodiment of the tracheostomy tube 100 with a plurality of pressure sensors 1000. A first pressure sensor 1000a may be positioned within the inner cuff 124, or alternatively, at the proximal end of its air tube (not shown), to measure the air pressure inside the inner cuff 124. A second pressure sensor 1000b is positioned inside the outer bladder 122, or alternatively, at the proximal end of its air tube (not shown), to measure the air pressure inside the outer bladder. One or more pressure sensors 1000c, 1000d may be positioned on an outer surface of the outer bladder 122 to measure a pressure that the cuff assembly applies to the tracheal wall (the "tracheal pressure"). In addition or alternately, a pressure sensor 1000e may be positioned between the outer bladder 122 and the inner cuff 124 t to measure the tracheal pressure.

A pressure regulation system monitors the tracheal pressure by utilizing the one or more pressure sensors 1000c,d on the outer bladder surface and/or the pressure sensor 1000e between the inner cuff 124 and outer bladder 122. For example, the force of the inner cuff 124 acts radially on the outer bladder 122 and is thus the force ultimately exerted on the trachea wall as the tracheal pressure. Since the intercuff pressure sensor 1000e is positioned between the inner cuff 124 and the outer bladder 122, it measures the radial force of the inner cuff 124 against the outer bladder 122. As such, the pressure sensor 1000e measures the tracheal pressure, e.g. the pressure exerted by the cuff assembly 102 against the tracheal wall.

The pressure sensors 1000 communicate pressure measurements to a pressure regulation system. The pressure sensors 1000 may include a wireless transmitter, such as a near field or radio frequency identification (RFID) transmitter or Internet of Things (IoT) cellular type transmitter. The pressure sensors may then wirelessly transmit pressure measurements to the pressure regulation system using the wireless transmitter.

Additional pressure sensor devices may be positioned within the tracheostomy tube 100 or at the tip of the tracheostomy tube 100, to measure the pressure of the oxygenated air delivered to a patient.

Figure 11:
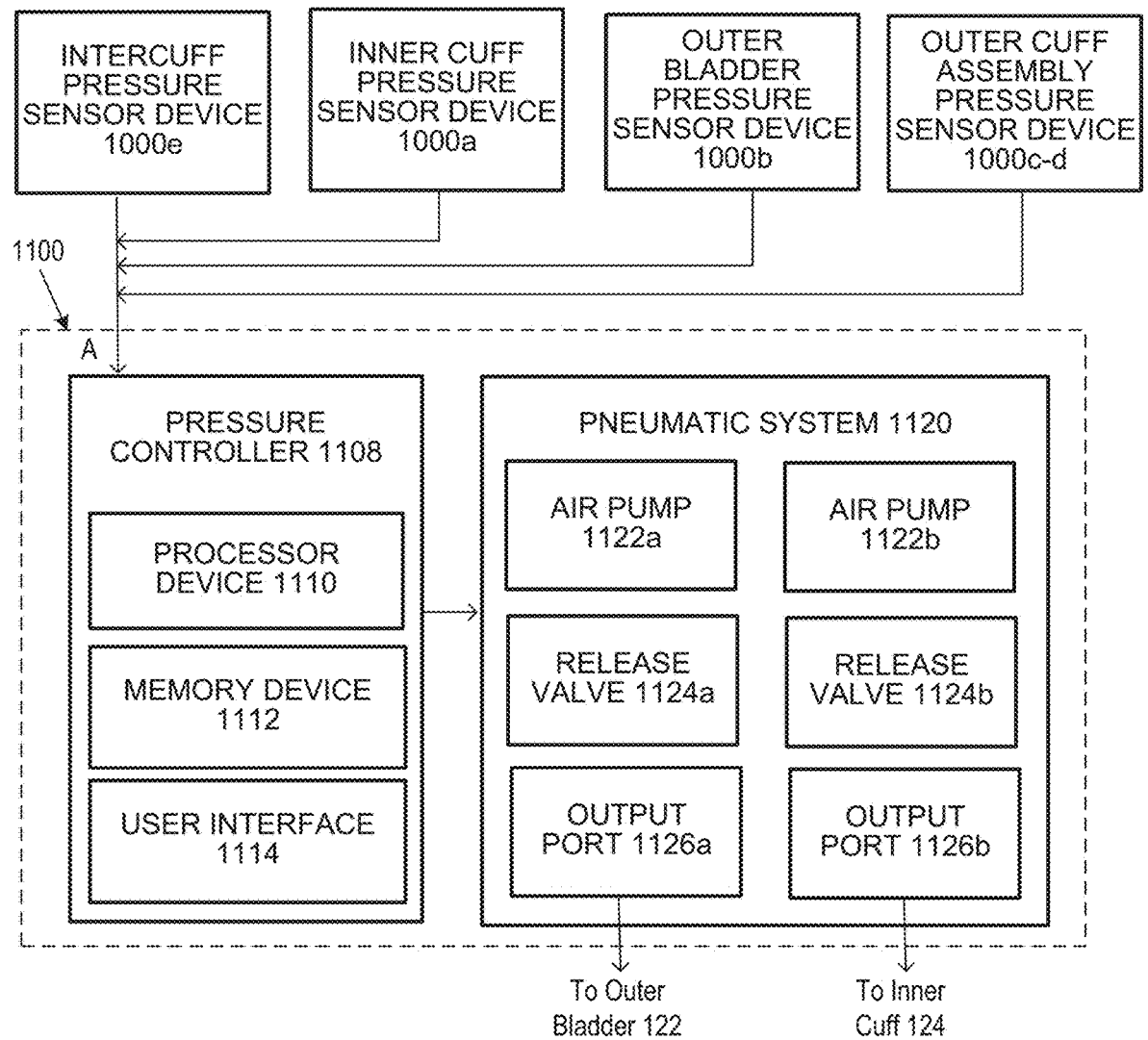
FIG. 11 illustrates a schematic block diagram of an exemplary embodiment of a pressure regulator and control system for the cuff assembly.

FIG. 11 illustrates a schematic block diagram of an exemplary embodiment of a pressure regulator and control system ("regulator system") 1100 for the cuff assembly 120. The regulator system 1100 fluidly communicates with and inflates and adjusts the pressure within the cuff assembly 120, e.g. when the tracheostomy tube 100 is implanted in a patient's trachea. The pressure of the inner cuff 124 and the outer bladder 122 of the cuff assembly 120 are monitored and controlled separately.

The regulator system 1100 includes a pressure controller 1108 and a pneumatic system 1120. The pressure controller 1108 includes a processor device 1110 and a memory device 1112. The memory device 1112 includes one or more non-transitory processor readable memories that store instructions which when executed by the processor device 1110 or other components of the regulator system 1100, causes the regulator system 1100 to perform one or more functions described herein. The processor device 1110 includes at least one processing circuit, such as a microprocessor, microcontroller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. The memory device 1112 includes a non-transitory memory device and may be an internal memory or an external memory, and may be a single memory device or a plurality of memory devices. The memory device 1112 may be a read-only memory, random access memory, volatile memory, non-volatile memory, static memory, dynamic memory, flash memory, cache memory, and/or any non-transitory memory device that stores digital information.

The pressure controller 1108 may be co-located with the pneumatic system 1120 in a same physical device or located separately in a different device or encasement. The pressure controller 1108 further includes a user interface 1114. The user interface 1114 generates user input and output (I/O) and includes one or more of a display, keyboard, touch screen, mouse, touchpad, gauge, switch, or other I/O device.

In use, a desired predetermined pressure setting is determined for the cuff assembly 120 by the pressure controller 1108 in response to user input received by the user interface 1114. Alternatively, a default pressure setting may be implemented, e.g. in absence of user input.

A different pressure setting may be set for the inner cuff 124 and the outer bladder 122. The pressure setting may be a predetermined pressure or a pressure range, e.g. typically within a plus or minus 2 cm H2O. For example, the pressure setting for the inner cuff 124 may be a pressure (plus or minus 2 cm H2O) within the range of 10 cm H2O to 20 cm H2O. In contrast, the pressure setting for the outer inflating bladder may be a pressure (plus or minus 2 cm H2O) within the range of 50 cm H2O to 150 cm H2O. The inner cuff 124 thus operates in a pressure range that is less than the operational pressure range of the outer bladder 122. The pressure controller 1108 further determines a frequency of measuring and adjusting the pressure of the cuff assembly 120, e.g. either through a user input or default setting.

The pneumatic system 1120 includes a first pneumatic pathway for the outer bladder 122 that includes a first air pump 1122a and a release valve 1124a that fluidly couples with the outer bladder 122 through, e.g., output port 1126a, a one way valve, pilot balloon, and inflation line 106b. The pneumatic system 820 further includes a different, second pneumatic pathway for the inner cuff 124 that includes a second air pump 1122b and release valve 1124b that fluidly couples with the inner cuff 124 through, e.g., output port 1126b, a one way valve, pilot balloon and inflation line 106a. Though two air pumps 1122a, 1122b are described herein, a single air pump may supply the pressurized air to the inner cuff 124 and the outer bladder 122, e.g. using a valve or switch between the two fluid pathways. The pneumatic system 1120 thus includes separate pneumatic pathways to fluidly increase or decrease the pressure in the air cuff 104 and the outer bladder 122 independently and separately.

In operation, the pressure controller 1108 receives pressure measurements from one or more pressure sensor devices 1000 to regulate the pressure of the cuff assembly 120. For example, the intercuff pressure sensor device 1000e is positioned between the inner cuff 124 and the outer bladder 122 and measures the radial force of the inner cuff 124 against the outer bladder 122. An inner cuff pressure sensor device 1000a may be positioned within the inner cuff 124 to measure the pressure within the inner cuff 124. An outer bladder pressure sensor device 1000b may be positioned to measure the pressure within the outer bladder 122. A further outer cuff assembly pressure sensor device 1000c and/or 1000d may be positioned on an outer surface of the outer bladder 122 to measure the tracheal pressure. Additional pressure sensor devices may also be implemented. The pressure sensor devices generate and communicate pressure measurements to the pressure controller 1108, e.g. either through a wired lead and/or a wireless transmitter.

The pressure regulator system 1100 includes a pressure feedback loop wherein the pressure controller 1108 controls the pneumatic system 1120 to adjust the pressures for both the inner cuff 124 and the outer bladder 122 responsive to the pressure measurements. The pressures of the inner cuff 124 and the outer bladder 122 are monitored and controlled separately. The pressure controller 1108 signals the pneumatic system 1120 to add or release air to the outer bladder 122 and/or the inner cuff 124. For example, to adjust the pressure in the outer bladder 122, the pressure controller 1108 may signal the air pump 1122a to add air to the outer bladder 122 or signal the release valve 1124a to release air from the outer bladder 122. In another example, to adjust the pressure in the inner cuff 124, the pressure controller 1108 may signal the air pump 1122b to add air to the inner cuff 124 or signal the release valve 1124b to release air from the inner cuff 124.

The regulator system 800 monitors the pressure measurements and adjusts the pressure, firstly of the outer bladder 122 and secondly of the inner cuff 124, automatically to achieve the predetermined pressure settings, e.g. preselected by an operator or by default. The pressure controller 1108 may monitor and adjust the pressure of the cuff assembly 120 continuously or may monitor and adjust the pressures at predetermined intervals. The regulator system 1100 may further include visible and/or audible alarms in the event of unsafe pressure measurements.

Figure 12:
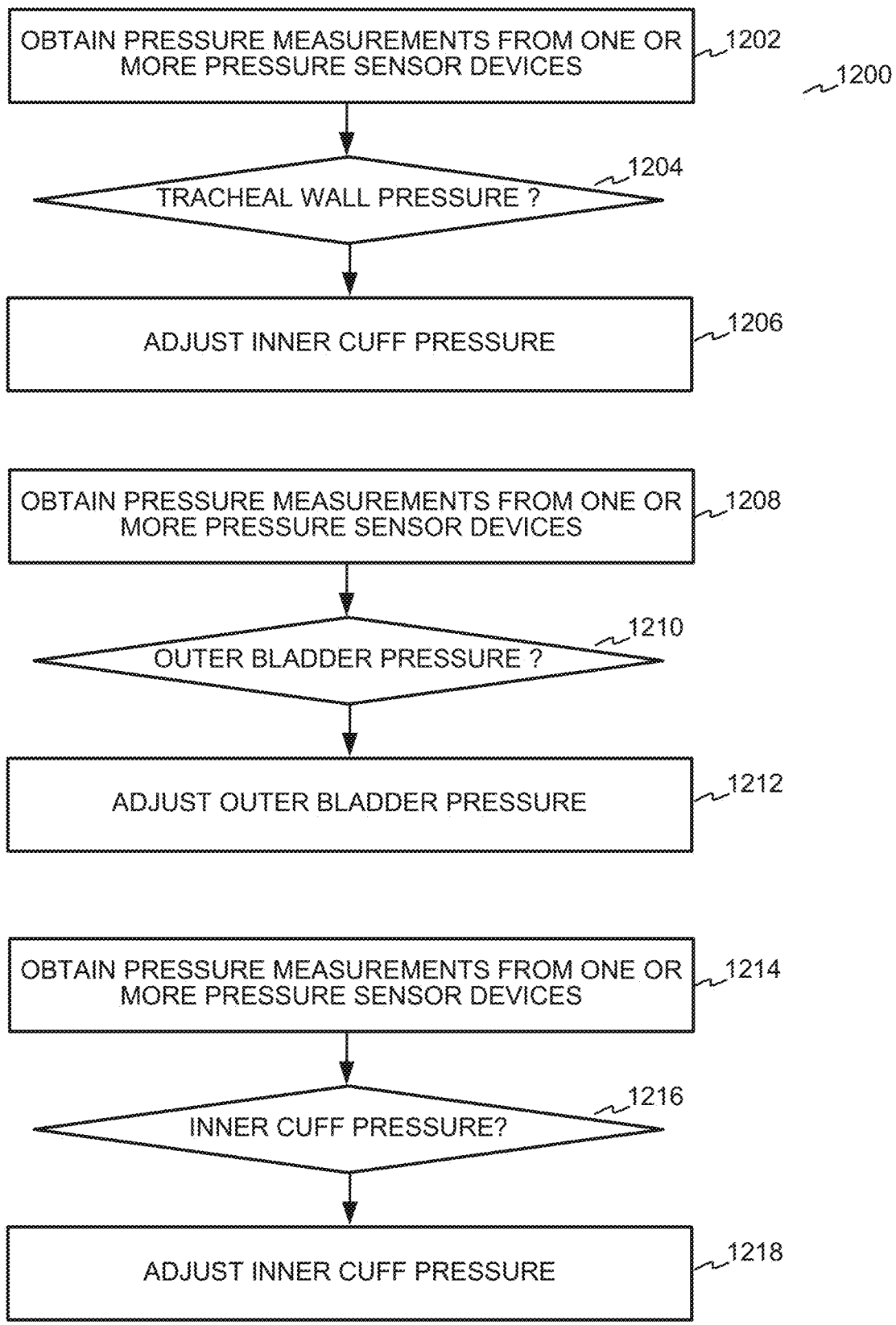
FIG. 12 illustrates a flow chart of an embodiment of one or more methods for monitoring and controlling the pressure of the cuff assembly.

FIG. 12 illustrates a flow chart of an embodiment of one or more methods 1200 for monitoring and controlling the pressure of the cuff assembly 120. At step 1202, one or more pressure measurements relating to the tracheal wall pressure are obtained by the regulator system 1100 from one or more pressure sensor devices 1000. Using these pressure measurements, the regulator system 1100 determines whether the tracheal pressure, e.g. the pressure exerted by the cuff assembly 120 on the tracheal wall, is within a predetermined pressure range at Step 1204. The pressure measurements may be from the intercuff pressure sensor device 1000e between the inner cuff 124 and the outer bladder 122 and/or from one or more pressure sensors 1000c-d located on an outer surface of the outer bladder 122. When the tracheal pressure exceeds a predetermined pressure range, the regulator system 1100 decreases at least the pressure in the inner cuff 124 at step 1106. For example, the regulator system 1100 may control the release valve 1124b to release air from the inner cuff 124. Since the tracheal mucosal blood flow may be compromised at applied pressures above 30 cm H2O (22 mmHg), when the measured tracheal pressure exceeds 30 cm H2O (22 mmHg), then the regulator system 1100 may decrease at least the pressure of the inner cuff 124.

When the tracheal pressure is less than a predetermined pressure range, the regulator system 1100 increases at least the pressure in the inner cuff 124 at Step 1206. For example, the regulator system 1100 may control the air pump 1122b to pump air into the inner cuff 124. In addition, the pressure of the outer bladder 122 may also be adjusted. These steps may be performed at preset intervals or continuously.

At step 1208, one or more pressure measurements relating to the outer bladder pressure are obtained by the regulator system 1100 from one or more pressure sensor devices. Using these pressure measurements, the regulator system 1100 determines whether the pressure of the outer bladder 122 is within a predetermined pressure range at step 1210. For example, the pressure measurements may be from a pressure sensor device 1000b located within the outer bladder 122 or at the pilot balloon for the inflation line 106b of the outer bladder 122. When the outer bladder pressure is less than or more than the predetermined pressure range, the regulator system 1100 increases or decreases the pressure in the outer bladder 122 at Step 1212. For example, the regulator system 800 may control the air pump 1122a to pump air into the outer bladder 122 when its pressure is below the predetermined pressure range or control the release valve 1124*a* to release air from the outer bladder 122 when its pressure is above the predetermined pressure range.

At step 1214, one or more pressure measurements relating to the inner cuff pressure are obtained by the regulator system 1100 from one or more pressure sensor devices. Using these pressure measurements, the regulator system 1100 determines whether the pressure of the inner cuff 124 is within a predetermined pressure range at step 1216. For example, the pressure measurements may be from a pressure sensor device 1000*a* located within the inner cuff 124 or at the pilot balloon of the inflation line 106*a* for the inner cuff 124. When the inner cuff pressure is less than or more than the predetermined pressure range, the regulator system 1100 may increase or decrease the pressure in the inner cuff 124 at Step 1218. For example, the regulator system 1100 may control the air pump 1122*b* to pump air into the inner cuff 124 when its pressure is below the predetermined pressure range or control the release valve 1124*b* to release air from the inner cuff 124 when its pressure is above the predetermined pressure range. The inner cuff is a low-pressure inflatable cuff and may have a predetermined pressure range of 10 cm H2O to 20 cm H2O.

The pressure of the inner cuff 124 and the outer bladder 122 of the cuff assembly 120 are thus controlled separately using separate pneumatic pathways, e.g., separate air pumps 1122 and/or release valves 1124 and separate air inflation tubes 106*a*, 106*b*. The pressure of the more inelastic outer bladder 122 is maintained at a higher pressure than the pressure of the more elastic inner cuff. The pressure controller 1110 may also independently adjust a pressure of the inner cuff 124 and/or the outer bladder 122 to adjust the tracheal pressure.

The cuff assembly 120 and the regulator system 1100 thus help to reduce microaspiration and infection of the lungs by maintaining a good seal with the tracheal wall but without unduly harming the tracheal wall. The systems provide an improved airway seal and cause a minimal damage to the airway.

The tracheostomy tube 100 described herein includes a novel secondary airflow opening 128 for reducing the risk of obstruction, an improved cuff assembly 120, and effective secretion collection and clearance system. The cuff assembly 120 comprises a torus-shaped outer bladder 122 and an inner cuff 124. The inner cuff is made with a relatively elastic material and operates at a lower pressure. The outer bladder 122 includes relatively less elastic material and operates at a higher pressure to achieve full inflation for an optimal tracheal seal.

The outer bladder 122 may also be configured to form a collection receptacle 700 at the superior aspect of the cuff system 120. Accumulated bodily secretions are then be evacuated via a suction channel from the receptacle 700.

The novel cuff system 120 disclosed herein further enables the length of the cuff to be significantly smaller than current tracheostomy cuffs. With a shorter cuff length, sufficient space is available in the distal segment of the tracheostomy tube 100 to create a secondary airflow opening 128 on the distal, lateral wall of the tracheostomy tube 100. The secondary airflow opening 128 provides an alternative means for respiration when the main opening 138 of a tracheostomy tube 100 becomes occluded. Without the secondary airflow opening 128, obstruction of a tracheostomy tube 100 may result in fatality. A tracheostomy tube 100 with a secondary airflow opening 128, improved cuff assembly 120, and effective secretion evacuation system disclosed herein represents a significant improvement for patient's safety and health.

As may be used herein, the term "operable to" or "configurable to" indicates that an element includes one or more of components, dimensions, circuits, instructions, modules, data, input(s), output(s), etc., to perform one or more of the described or necessary corresponding functions and may further include inferred coupling to one or more other items to perform the described or necessary corresponding functions. As may also be used herein, the term(s) "coupled," "coupled to," "connected to" and/or "connecting" or "interconnecting" includes direct connection or link between components or between nodes/devices and/or indirect connection between components or nodes/devices via an intervening item. As may further be used herein, inferred connections (i.e., where one element is connected to another element by inference) includes direct and indirect connection between two items in the same manner as "connected to." As may be used herein, the terms "substantially" and "approximately" provides an industry-accepted tolerance for its corresponding term and/or relativity between items.

Note that the aspects of the present disclosure may be described herein as a process that is depicted as a schematic, a flowchart, a flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed. A process may correspond to a method, a function, a procedure, a subroutine, a subprogram, etc. When a process corresponds to a function, its termination corresponds to a return of the function to the calling function or the main function.

The various features of the disclosure described herein can be implemented in different systems and devices without departing from the disclosure. It should be noted that the foregoing aspects of the disclosure are merely examples and are not to be construed as limiting the disclosure. The description of the aspects of the present disclosure is intended to be illustrative, and not to limit the scope of the claims. As such, the present teachings can be readily applied to other types of apparatuses and many alternatives, modifications, and variations will be apparent to those skilled in the art.

In the foregoing specification, certain representative aspects have been described with reference to specific examples. Various modifications and changes may be made, however, without departing from the scope of the present invention as set forth in the claims. The specification and figures are illustrative, rather than restrictive, and modifications are intended to be included within the scope of the claims. Accordingly, the scope of the claims should be determined by the descriptions herein and their legal equivalents rather than by merely the examples described. For example, the components and/or elements recited in any apparatus claims may be assembled or otherwise operationally configured in a variety of permutations and are accordingly not limited to the specific configuration recited in the claims.

Furthermore, certain benefits, other advantages and solutions to problems have been described above with regard to particular embodiments; however, any benefit, advantage, solution to a problem, or any element that may cause any particular benefit, advantage, or solution to occur or to become more pronounced are not to be construed as critical, required, or essential features or components of any or all the claims.

As used herein, the terms "comprise," "comprises," "comprising," "having," "including," "includes" or any variation thereof, are intended to reference a nonexclusive inclusion, such that a process, method, article, composition or apparatus that comprises a list of elements does not include only those elements recited, but may also include other elements not expressly listed or inherent to such process, method, article, composition, or apparatus. Other combinations and/or modifications of the above-described structures, arrangements, applications, proportions, elements, materials, or components used in the practice of the present invention, in addition to those not specifically recited, may be varied or otherwise particularly adapted to specific environments, manufacturing specifications, design parameters, or other operating requirements without departing from the general principles of the same.

Moreover, reference to an element in the singular is not intended to mean "one and only one" unless specifically so stated, but rather "one or more." Unless specifically stated otherwise, the term "some" refers to one or more. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is intended to be construed under the provisions of 35 U.S.C. § 112(f) as a "means-plus-function" type element, unless the element is expressly recited using the phrase "means for" or, in the case of a method claim, the element is recited using the phrase "step for."

The invention claimed is:

1. A tracheostomy tube, comprising:
    an outer cannula of the tracheostomy tube including a distal segment, wherein the distal segment includes a main distal opening;
    a cuff assembly of the tracheostomy tube at the distal segment of the outer cannula, including:
        an inflatable inner cuff with an inner surface and an outer surface, wherein the inner surface is positioned adjacent to the outer cannula and wherein the inner cuff has a first elasticity; and
        an inflatable outer bladder positioned adjacent to the outer surface of the inner cuff, wherein the outer bladder has a second elasticity that is less than the first elasticity of the inner cuff; and
    wherein the distal segment of the outer cannula of the tracheostomy tube forms a secondary airflow opening between the cuff assembly and the main distal opening, wherein the secondary airflow opening between the cuff assembly and the main distal opening of the tracheostomy tube has a sufficient total area to maintain airflow for respiration of a patient and is configured to remain open and to serve as a conduit for both inspiratory and expiratory air to flow during ventilation.

2. The tracheostomy tube of claim 1, wherein a length of the cuff assembly $L_{CA}$ is from 10 millimeters (mm) to 20 mm and the secondary airflow opening is formed on a lateral wall of the distal segment of the outer cannula between the cuff assembly and the main distal opening and has a total area of at least 20 square mm.

3. The tracheostomy tube of claim 1, wherein the secondary airflow opening comprises a plurality of openings formed on the lateral wall of the distal segment of the outer cannula between the cuff assembly and the main distal opening.

4. The tracheostomy tube of claim 3, wherein the plurality of openings each have slanted walls, wherein an interior opening of each of the plurality of openings is more distal than an exterior opening of each of the plurality of openings.

5. The tracheostomy tube of claim 1, wherein the secondary airflow opening, upon blockage of the main distal opening of the tracheostomy tube, functions as a main conduit through which the air flows from the patient to a ventilator and from the ventilator to the patient.

6. The tracheostomy tube of claim 1, further comprising:
    an inner cannula positioned internally to the outer cannula, wherein the inner cannula forms a first plurality of openings.

7. The tracheostomy tube of claim 6, wherein the secondary airflow opening formed in the outer cannula comprises:
    at least one opening that substantially exposes the plurality of openings formed in the inner cannula.

8. The tracheostomy tube of claim 6, wherein the secondary airflow opening formed in the outer cannula comprises:
    a second plurality of openings formed in the outer cannula that substantially align with the first plurality of openings formed in the inner cannula.

9. The tracheostomy tube of claim 1, further comprising:
    a suction channel formed internally to the tracheostomy tube, including a distal end in proximity to a proximal side of the cuff assembly and a proximal end of the suction channel at a proximal end of the tracheostomy tube, wherein the proximal end of the suction channel is in fluid communication with a vacuum.

10. The tracheostomy tube of claim 1, further comprising:
    a pressure regulator configured to:
        adjust a first pressure in the inner cuff using a first pneumatic pathway, wherein the first pressure is within a first pressure range of 10 cm H2O to 20 cm H2O; and
        adjust a second pressure in the outer bladder using a different, second pneumatic pathway, wherein the second pressure is within a second pressure range of 50 cm H2O to 150 cm H2O.

11. A tracheostomy tube, comprising:
    a cuff assembly of the tracheostomy tube, wherein the cuff assembly has a length of no more than 20 mm, including:
        an inflatable inner cuff with an inner surface and an outer surface; and
        an inflatable outer bladder positioned adjacent to the outer surface of the inner cuff, wherein the outer bladder has a second elasticity that is less than the first elasticity of the inner cuff;
    an outer cannula of the tracheostomy tube including a distal main opening, wherein an inner surface of the cuff assembly is positioned adjacent to the outer cannula and wherein the outer cannula has a length of at least 10 mm between the cuff assembly and the distal main opening; and
    wherein the outer cannula forms a secondary airflow opening between the cuff assembly and the main distal opening, wherein the secondary airflow opening is configured to remain open during ventilation.

12. The tracheostomy tube of claim 11, wherein the secondary airflow opening is formed on a lateral wall of the distal segment of the outer cannula between the cuff assembly and the main distal opening and has a total area sufficient to maintain airflow for respiration of a patient of at least 20 square mm.

13. The tracheostomy tube of claim 11, further comprising:
an inner cannula positioned internally to the outer cannula, wherein the inner cannula forms a plurality of openings and wherein the secondary airflow opening formed in the outer cannula substantially exposes the first plurality of openings in the inner cannula.

14. The tracheostomy tube of claim 11, further comprising:
an inner cannula positioned internally to the outer cannula, wherein the inner cannula forms a first plurality of openings; and
wherein the secondary airflow opening in the outer cannula comprises a second plurality of openings, wherein the second plurality of openings in the outer cannula substantially align with the first plurality of openings in the inner cannula.

15. The tracheostomy tube of claim 11, further comprising:
a first inflation channel formed in a wall of the outer cannula, wherein the first inflation channel extends from at least a flange of the outer cannula to the cuff assembly and wherein a first inflation line for inflating the inner cuff is positioned in the first inflation channel;
a second inflation channel formed in the wall of the outer cannula, wherein the second inflation channel extends from at least the flange of the outer cannula to cuff assembly and wherein a second inflation line for inflating the outer bladder is positioned in the second inflation channel; and
a pressure regulator system configured to:
maintain a first pressure range within the inner cuff first pressure using the first inflation channel to add or remove air from the inner cuff; and
maintain a second pressure range within the outer bladder using the second inflation channel to add or remove air from the outer bladder.

16. The tracheostomy tube of claim 11, further comprising:
a suction channel formed within a wall of the outer cannula, wherein the suction channel extends from a proximal side of the cuff assembly to a proximal side of a flange of the tracheostomy tube;
a secretion collection receptacle positioned at the proximal side of the cuff assembly, wherein the secretion collection receptacle includes a top portion of the outer bladder that extends proximally from a proximal surface of the inner cuff forming a trough for collection of secretions; and
a suction catheter positioned in the suction channel, wherein the suction catheter extends from the suction channel through an opening in the outer cannula into the secretion collection receptacle.

17. The tracheostomy tube of claim 11, wherein the inner cuff comprises a relatively elastic material, wherein the relatively elastic material includes one or more of: rubber, silicone, latex, polyvinyl chloride (PVC), neoprene, polyisoprene, or polyurethane (PU); and
wherein the outer bladder comprises a relatively inelastic material, wherein the relatively inelastic material includes one or more of: polyethylene teraphthalate (PETP), low-density polyethylene (LDPE), polyvinyl chloride (PVC), silicone, neoprene, polyisoprene, or polyurethane (PU).

18. The tracheostomy tube of claim 11, wherein a length of the inner cuff is in the range of 10 mm to 20 mm, and wherein a length of the outer bladder is in the range of 5 mm to 9 mm.

19. The tracheostomy tube of claim 11, wherein the inner cuff and outer bladder are shaped cylindrical or toroidal.

20. A tracheostomy tube configured to fit within a trachea, comprising:
a cuff assembly including at least one inflatable cuff;
an outer cannula including a distal main opening, wherein an inner surface of the cuff assembly is positioned adjacent to the outer cannula and wherein the outer cannula forms at least one secondary airflow opening between the cuff assembly and the main distal opening; and
an inner cannula positioned internally to the outer cannula, wherein the inner cannula forms a first plurality of openings, wherein the at least one secondary airflow opening in the outer cannula substantially exposes the first plurality of openings in the inner cannula.

21. The tracheostomy tube of claim 20, wherein the secondary airflow opening formed in the outer cannula comprises at least one of:
at least one opening that substantially exposes the plurality of openings formed in the inner cannula; or
a second plurality of openings formed in the outer cannula that substantially align with the first plurality of openings formed in the inner cannula.

22. A tracheostomy tube configured to fit within a trachea, comprising:
at least one inflatable cuff; and
a first cannula including at least one main distal opening, wherein the first cannula forms at least one secondary airflow opening between the at least one inflatable cuff and the at least one main distal opening, wherein the at least one secondary airflow opening is configured to remain open for inhalation and exhalation during ventilation and includes a total area sufficient to maintain airflow for respiration of a patient; and
wherein a length of the at least one inflatable cuff creates a distance between the at least one inflatable cuff and the main distal opening sufficient to fit the secondary airflow opening having the total area sufficient to maintain the airflow for respiration of the patient.

23. The tracheostomy tube of claim 22, wherein the at least one secondary airflow opening comprises a plurality of openings formed on a lateral wall of the first cannula between the cuff assembly and the main distal opening.

24. The tracheostomy tube of claim 22, wherein the tracheostomy tube further comprises:
an inner cannula configured to fit internally to the first cannula, wherein the inner cannula forms one or more lateral openings, wherein the at least one secondary airflow opening in the first cannula substantially exposes the one or more lateral openings in the inner cannula.

25. The tracheostomy tube of claim 22, wherein the length of the at least one inflatable cuff is at most 20 mm and wherein the total area of the secondary airflow opening is at least 20 square mm and wherein the distance between the at least one inflatable cuff and the main distal opening is at least 10 mm.

* * * * *